(12) United States Patent
O'Bryant

(10) Patent No.: US 11,885,816 B2
(45) Date of Patent: *Jan. 30, 2024

(54) PERSONALIZED MEDICINE APPROACH FOR TREATING COGNITIVE LOSS

(71) Applicant: University of North Texas Health Science Center at Fort Worth, Fort Worth, TX (US)

(72) Inventor: Sid E. O'Bryant, Aledo, TX (US)

(73) Assignee: University of North Texas Health Science Center at Forth Worth, Forth Worth, TX (US)

( * ) Notice: Subject to any disclaimer, the term of this patent is extended or adjusted under 35 U.S.C. 154(b) by 158 days.

This patent is subject to a terminal disclaimer.

(21) Appl. No.: 15/037,492

(22) PCT Filed: Nov. 26, 2014

(86) PCT No.: PCT/US2014/067562
§ 371 (c)(1),
(2) Date: May 18, 2016

(87) PCT Pub. No.: WO2015/081166
PCT Pub. Date: Jun. 4, 2015

(65) Prior Publication Data
US 2016/0291036 A1 Oct. 6, 2016

Related U.S. Application Data

(60) Provisional application No. 61/908,812, filed on Nov. 26, 2013.

(51) Int. Cl.
| | |
|---|---|
| *G01N 33/68* | (2006.01) |
| *G16B 40/00* | (2019.01) |
| *C12Q 1/6883* | (2018.01) |
| *G16H 50/20* | (2018.01) |
| *G16B 40/20* | (2019.01) |
| *G16B 40/30* | (2019.01) |
| *G16H 50/30* | (2018.01) |

(52) U.S. Cl.
CPC ....... *G01N 33/6896* (2013.01); *C12Q 1/6883* (2013.01); *G16B 40/00* (2019.02); *G16B 40/20* (2019.02); *G16B 40/30* (2019.02); *G16H 50/20* (2018.01); *G16H 50/30* (2018.01); *C12Q 2600/106* (2013.01); *C12Q 2600/158* (2013.01); *G01N 2800/2814* (2013.01); *G01N 2800/52* (2013.01); *G01N 2800/60* (2013.01); *G01N 2800/7095* (2013.01)

(58) Field of Classification Search
None
See application file for complete search history.

(56) References Cited

U.S. PATENT DOCUMENTS

| | | |
|---|---|---|
| 5,192,753 A | 3/1993 | McGeer et al. |
| 6,819,956 B2 | 11/2004 | Dilorenzo |
| 7,598,049 B2 | 10/2009 | Ray et al. |
| 8,008,025 B2 | 8/2011 | Zhang |
| 8,430,816 B2 | 4/2013 | Avinash et al. |
| 2006/0094064 A1 | 5/2006 | Sandip et al. |
| 2009/0075395 A1 | 3/2009 | Lee et al. |
| 2010/0124756 A1 | 5/2010 | Ray |
| 2010/0233818 A1 | 9/2010 | Sekiyama |
| 2010/0280562 A1* | 11/2010 | Pi .................. C12Q 1/6883 607/2 |
| 2011/0082187 A1 | 4/2011 | Campbell et al. |
| 2011/0159527 A1 | 6/2011 | Schlossmacher et al. |
| 2011/0172501 A1 | 7/2011 | Antonijevic |
| 2011/0202284 A1 | 8/2011 | Mcreynolds |
| 2012/0238835 A1 | 9/2012 | Hyde et al. |
| 2012/0238837 A1 | 9/2012 | Hyde et al. |
| 2012/0295281 A1 | 11/2012 | Rai et al. |
| 2013/0012403 A1 | 1/2013 | Hu |
| 2014/0018446 A1 | 1/2014 | Royall et al. |
| 2014/0147863 A1 | 5/2014 | O'Bryant et al. |
| 2014/0220568 A1* | 8/2014 | Inze .................. A01H 1/00 435/6.11 |
| 2014/0315736 A1 | 10/2014 | Nagele |
| 2015/0086616 A1 | 3/2015 | Lehrer |

(Continued)

FOREIGN PATENT DOCUMENTS

| | | |
|---|---|---|
| JP | 2007513337 | 5/2007 |
| JP | 2009540309 | 11/2009 |

(Continued)

OTHER PUBLICATIONS

Thaker (Expert Opinion of Therapeutic Targets 11:9 pages 1189-1206 Pub online Sep. 11, 2007).*
Colangelo (Journal of Neuroscience Research 70:462-473 2002).*
Chan (G&P magazine 2006 vol. 6 No. 3 pp. 20-26).*
Whitehead (Genome Biology 2005 vol. 6 Issue 2 Article R13).*
Coleman (Drug Discovery Today. 2003. 8: 233-235).*
Swardfager (Biol Psychiatry 2010 vol. 68 pp. 930-941).*
Leung (PLOS ONE Jun. 3, 2013 vol. 8 Issue 6 e64971 pp. 1-10).*
Koyama (J Gerontol A Biol Sci Med Sci Apr. 2013 vol. 68 Issue 4 pp. 433-440).*

(Continued)

*Primary Examiner* — Amanda Haney
(74) *Attorney, Agent, or Firm* — Domingos J. Silva; Saul Ewing LLP

(57) ABSTRACT

The present invention includes methods for selecting a therapy for improved cognition as well as prevention of cognitive loss/dysfunction using one or more endophenotypes comprising: obtaining a sample from a subject; measuring biomarkers that differentiate between an inflammatory, a metabolic, a neurotrophic, and a depressive endophenotype; and selecting a course of treatment for the subject based on whether the subject is scored as having a high or a low endophenotype for one or more of the inflammatory, a metabolic, a neurotrophic, and a depressive endophenotypes.

8 Claims, 7 Drawing Sheets

(56) References Cited

U.S. PATENT DOCUMENTS

| | | |
|---|---|---|
| 2015/0241454 A1 | 8/2015 | Sandip et al. |
| 2016/0154010 A1 | 6/2016 | O'Bryant et al. |
| 2016/0291036 A1 | 10/2016 | O'Bryant |
| 2017/0014436 A1 | 1/2017 | Fayad |
| 2017/0356903 A1 | 12/2017 | Domenyuk et al. |
| 2019/0219599 A1 | 7/2019 | O'Bryant et al. |
| 2019/0234967 A1 | 8/2019 | O'Bryant |
| 2020/0078366 A1 | 3/2020 | Elmaleh |
| 2020/0147069 A1 | 5/2020 | Cohen |
| 2021/0215720 A1 | 7/2021 | O'Bryant |

FOREIGN PATENT DOCUMENTS

| | | |
|---|---|---|
| JP | 2010019851 | 1/2010 |
| JP | 2011093941 | 5/2011 |
| JP | 2012523009 | 9/2012 |
| WO | 9840061 A1 | 9/1998 |
| WO | 2006020269 A2 | 2/2006 |
| WO | 2007094472 A1 | 8/2007 |
| WO | 2007144194 A1 | 12/2007 |
| WO | 20100118035 A2 | 10/2010 |
| WO | 2011143597 A1 | 11/2011 |
| WO | 2014066318 A1 | 5/2014 |
| WO | 2015006489 A1 | 1/2015 |
| WO | 2015006489 A8 | 1/2015 |
| WO | 2015081166 A1 | 6/2015 |
| WO | 2017223291 A1 | 12/2017 |
| WO | 2019143562 A1 | 7/2019 |

OTHER PUBLICATIONS

Richartz (Journal of Psychiatric Research 39 2005 pp. 535-543).*
Green (Clinical Cornerstone Sports Medicine vol. 3 No. 5 2001).*
Pujos (Anal Bioanal Chem 2005 381:244-254).*
Prasad (Cardiovascular Drug Reviews vol. 24 No. 1 pp. 33-50 2006).*
Lista (Progress in Neurobiology 101-102 (2013) pp. 1-17 Pub online Jun. 26, 2012).*
Trepanier (Journal of Alzheimer's Disease 21 2010 1089-1099).*
Yokono, Koichi, "Alzheimer Disease as a diabetic complication," Japanese Journal of Geriatrics, 2010, vol. 47, pp. 385-389.
Braskie, M.N., et al., "Neuroimaging measures as endophenotypes in Alzheimer's disease," International Journal of Alzheimer's Disease, Feb. 7, 2011, 16 pp.
During, E.H., et al., "The concept of FDG-PET endophenotype in Alzheimer's disease," Neurol Sci., Aug. 2011, vol. 32, pp. 559-569.
Gottesman, I.I., et al., "The endophenotype concept in psychiatry: etymology and strategic intentions," American Journal of Psychiatry, Apr. 2003; 160(4), pp. 636-645.
Janocko N.J., et al., "Neuropathologically defined subtypes of Alzheimer's disease differ significantly from heurofibrillary tangle-predominant dementia," Acta Neuropathologica, Nov. 2012, vol. 124(5), pp. 681-692.
Johnson L.A., et al., "A Depressive Endophenotype of Mild Cognitive Impairment and Alzheimer's Disease," PLoS ONE, Jul. 2013, vol. 8:7, e68848, 8 pp.
O'Bryant, S.E., et al., "Brain-Derived Neurotrophic Factor Levels in Alzheimer's Disease," J. Alzheimers Dis., Jun. 2009, vol. 17(2), pp. 337-341.
O'Bryant, S.E., et al., "Decreased C-Reactive Protein Levels in Alzheimer Disease," J. Geriatr. Psychiatry Neurol., Mar. 2010, vol. 23(1), pp. 49-53.
O'Bryant, S.E., et al., "A Serum Protein-Based Algorithm for the Detection of Alzheimer Disease," Arch. Neurol., Sep. 2010, vol. 67(9), pp. 1077-1081.
O'Bryant, S.E., et al., "A Blood-Based Algorithm for the Detection of Alzheimer's Disease," Dement Geriatr Cogn Disord., Aug. 24, 2011, vol. 32, pp. 55-62.
O'Bryant, S.E., et al., "A Blood-Based Screening Tool for Alzheimer's Disease that Spans Serum and Plasma: Findings from TARC and ADNI," PLoS ONE, Dec. 7, 2011, vol. 6:12, e28092, 8 pp.

O'Bryant, S.E., et al., "Serum Brain-Derived Neurotrophic Factor Levels Are Specifically Associated with Memory Performance among Alzheimer's Disease Cases," Dement Geriatr Cogn Disord., Dec. 7, 2010, vol. 31, pp. 31-36.
O'Bryant, S.E., et al., "Biomarkers of Alzheimer's Disease Among Mexican Americans," J. Alzheimers Dis., Jan. 1, 2013, vol. 34(4), pp. 841-849.
International Search Report and Written Opinion of KIPO for PCT/US2014/067562 dated Mar. 6, 2015, 12 pp.
Laske, et al., "Immune Profiling in Blood Identifies sTNF-R1 Performing Comparably Well as Biomarker Panels for Classification of Alzheimer's Disease Patients." Journal of Alzheimer's Disease, Jan. 2013, vol. 34, No. 2, pp. 367-375.
Extended European Search Report for 14865107.8 dated Jul. 24, 2017, 12 pages.
O'Bryant S.E., et al., "Biomarkers of Alzheimer's Disease Among Mexican Americans," J. Alzheimers Dis., vol. 34 (4), Dec. 2012, pp. 841-849.
Alzheimer's Association: "Alzheimer's Disease Facts and Figures", Alzheimer's & Dementia vol. 9, Issue 2, Mar. 2013, pp. 208-245.
Belmin J., et al., "Assessment and Management of Patients with Cognitive Impairment and Dementia in Primary Care." The Journal of Nutrition, Health & Aging, vol. 16, Nov. 5, 2012, pp. 462-467.
Benadiba M., et al., "New Molecular Targets for PET and SPECT Imaging in Neurodegenerative Diseases," Rev. Bras. Psiquiatr., Oct. 2012;34 (Suppl2):S125-S148.
Bjerke M., et al., "Confounding Factors Influencing Amyloid Beta Concentration in Cerebrospinal Fluid," International Journal of Alzheimer's Disease, vol. 2010, Jun. 7, 2010, pp. 1-11.
Breiman L., "Random Forests" Learning Machines, Oct. 2001, vol. 45, Issue 1, pp. 5-32.
Dickstein DL., et al., "Role of Vascular Risk Factors and Vascular Dysfunction in Alzheimer's Disease," Mt. Sinai. J. Med., 77(1), Aug. 2010, pp. 82-102.
Duff K., et al., "Utility of the RBANS in Detecting Cognitive Impairment Associated with Alzheimer's Disease Sensitivity, Specificity, and Positive and Negative Predictive Powers," Archives of Clinical Neuropsychology 23 (2008) pp. 603-612.
Duff K., et al., "Diagnostic Accuracy of the RBANS in Mild Cognitive Impairment: Limitations on Assessing Milder Impairments," Archives of Clinical Neuropsychology, vol. 25, Jun. 21, 2010, pp. 429-441.
Edwards, M., et al, "Combining Select Neuropsychological Assessment with Blood-Based Biomarkers to Detect Mild Alzheimer's Disease: A Molecular Neuropsychology Approach," Journal of Alzheimer's Disease, vol. 42, Apr. 2014, pp. 635-640.
Hall, J. R., et al., "Biomarkers of Vacular Risk, Systemic Inflammation, and Microvascular Pathology and Neuropsychiatric Symptoms in Alzheimer's Disease," Journal of Alzheimer's Disease, vol. 35, Jan. 2013, pp. 363-371.
International Search Report and Written Opinion of KIPO for PCT/US2014/046015 dated Oct. 22, 2014, 15 pp.
Johnson, L. A., et al., "Comorbid Depression and Diabetes as a Risk for Mild Cognitive Impairment and Alzheimer's Disease in Elderly Mexican Americans," Journal of Alzheimer's Disease, vol. 47, Apr. 2015, pp. 129-136.
Kounnas MZ., et al., "Modulation of g-Secretase Reduces b-Amyloid Deposition in a Transgenic Mouse Model of Alzheimer's Disease," Neuron 67, Sep. 9, 2010, pp. 769-780.
Laske C., et al., "Identification of a Blood-based Biomarker Panel for Classification of Alzheimer's Disease," International Journal of Neuropsychopharmacology, Feb. 12, 2011, pp. 1147-1155.
Lopponen M., et al., "Diagnosing cognitive impairment and dementia in primary health care—a more active approach is needed," Age and Ageing vol. 32:6, Apr. 2003, pp. 606-612.
Martin MA, et al., "Recruitment of Mexican-American Adults for an Intensive Diabetes Intervention Trial," Ethnicity and Disease, 21(1), 2011, pp. 7-12.
Mckhann G., et al., "Clinical diagnosis of Alzheimer's disease: Report of the NINCDS-ADRDA Work Group* under the auspices of Department of Health and Human Services Task Force on Alzheimer's Disease," Neurology, vol. 34, Jul. 1984, pp. 939-944.

(56) References Cited

OTHER PUBLICATIONS

O'Bryant S.E., et al., "Discrepancies between self-reported years of education and estimated reading level among elderly community-dwelling African-Americans: Analysis of the MOAANS data," Archives of Clinical Neuropsychology, vol. 22, 2007, pp. 327-332.
O'Bryant S.E., et al., "A Serum Protein-Based Algorithm for the Detection of Alzheimer's Disease," Arch Neurol., Sep. 13, 2010, vol. 67(9), pp. 1077-1081.
O'Bryant, S.E., et al., "Characterization of Mexican Americans with Mild Cognitive Impairment and Alzheimer's Disease," Journal of Alzheimer's Disease, vol. 33, Aug. 2012, pp. 373-379.
O'Bryant, S.E., et al., "Comparing biological markers of Alzheimer's Disease Across Blood Fraction and Platforms: Comparing Apples to Oranges," Alzheimer's & Dementia: Diagnosis, Assessment & Disease Monitoring, vol. 3, 2016, pp. 27-34.
O'Bryant, S.E., et al., "Guidelines for the Standarization of Preanalytic Variables for Blood-Based Biomarker Studies in Alzheimer's Disease Research," Alzheimer's & Dementia, 2014, pp. 1-12.
O'Bryant, S.E., et al., "Molecular Neuropsychology: Creation of Test-Specific Blood Biomarker Algorithms," Dement. Geriatr. Cogn. Disord., Oct. 2013, vol. 37, pp. 45-47.
O'Bryant S.E., et al., "Manuscript in Press: Dementia & Geriatric Cognitive Disorders: Molecular Neuropsychology: Creation of Test-Specific Blood Biomarker Algorithms," Dement. Geriatr. Cogn. Disord., Apr. 17, 2015, 37(0), pp. 45-57.
O'Bryant S.E., et al., "Validation of a serum screen for Alzheimer's disease across assay platforms, species and tissues," Journal of Alzheimer's Disease, vol. 42, No. 4, Jan. 1, 2014, pp. 1325-1335.
Oh E.S., et al., "Comparison of Conventional ELISA with Electrochemiluminescence Technology for Detection of Amyloid-B in Plasma," J. Alzheimers Dis., 2010, vol. 21(3), pp. 769-773.
Okereke O.I., et al., "A profile of impaired insulin degradation in relation to late-life cognitive decline: A preliminary investigation," Int. J. Geriatr. Phsychiatry, Feb. 2009, vol. 24(2), pp. 177-182.
Reddy M.M., et al., "Identification of Candidate IgG Biomarkers for Alzheimer's Disease via Combinatorial Library Screening," Cell (144), Jan. 7, 2011, pp. 132-142.
Swardfager, et al., "A meta-analysis of cytokines in Alzheimer's disease," Biological Psychiatry, vol. 68, No. 10, 2010, pp. 930-941.
Thal L.J., et al., "The Role of Biomarkers in Clinical Trials for Alzheimer Disease," Alzheimer Dis. Assoc. Disord., 2006, vol. 20(1), pp. 6-15.
Barber, R., et al. (Guanghua Xiao), "An Inflammatory Endophenotype of Alzheimer's Disease," Poster Presentation, Alzheimer's and Dementia 2010, 6(f) Supplement: S530, 1 pg.
Humpel, Christian, "Identifying and validating biomarkers for Alzheimer's disease," Trends in Biotechnology, Jan. 2011, vol. 29, No. 1, pp. 26-32.
International Search Report and Written Opinion of KIPO for PCT/US2017/038712 dated Sep. 20, 2017, 16 pp.
Thaker, G., "Schizophrenia Endophenotypes as Treatment Targets," Expert Opin Ther Targets (2007), 11 (9):1189-1206.
Doecke, J.D., et al., "Blood-Based Protein Biomarkers for Diagnosis of Alzheimer Disease," Arch. Neurol., vol. 69 (10), Jul. 16, 2012, pp. 1318-1325.
Extended European Search Report for 14822061.9 dated Nov. 23, 2016, 12 pp.
Anonymous "Clinical and neuropathological criteria for frontotemporal dementia" The Lund and Manchester Groups. Journal Of Neurology, Neurosurgery, and Psychiatry. 1994;57(4 (Print)):416-418.
Arora, et al. "Diagnostic accuracy of point-of-care testing for diabetic ketoacidosis at emergency-department triage: B-hydroxybutyrate versus the urine dipstick" Diabetes Care. Apr. 2011;34(4):852-854.
Australian Government, IP Australia, 1st Examination Report for Australian Patent Appl. No. 2017268567 dated Feb. 15, 2019, 4 pp.
Bandason, et al. "Validation of a screening tool to identify older children living with HIV in primary care facilities in high HIV prevalence settings" AIDS. 2016;30(5):779-785.
Biomarkers Definitions Working Group "Biomarkers and surrogate endpoints: preferred definitions and conceptual framework" Clin Pharmacol Ther 69:89-95. Mar. 2001.
Birrer, et al. "Depression in later life: A diagnostic and therapeutic challenge" American Family Physician. May 2004;69(10):2375-2382.
Bjerke, et al., "Confounding Factors Influencing Amyloid Beta Concentration in Cerebrospinal Fluid," International Journal of Alzheimer's Disease, vol. 2010, Jun. 7, 2010, pp. 1-11.
Canadian Intellectual Property Office, Examination Report for Canadian Appl. No. 2,920,474 dated Apr. 3, 2017, 4 pp.
Canadian Intellectual Property Office, Examination Report for Canadian Appl. No. 2,920,474 dated Oct. 15, 2018, 5 pp.
Chan, et al., "Expression Analyses and molecular biological studies contribute to a systems-level understanding of host response, and new analytical software tools can help," Drug Discovery & Development, Apr. 1, 2006, pp. 1-4.
Cruchaga, C., "Cerebrospinal fluid APOE levels: an endophenotype for genetic studies for Alzheimer's disease," Human Molecular Genetics. Jul. 13, 2012, pp. 1-14.
Dickstein, et al., "Role of Vascular Risk Factors and Vascular Dysfunction in Alzheimer's Disease," Mt. Sinai. J. Med., 77(1), Aug. 2010, pp. 82-102.
Elsafi, et al. "The sensitivity, specificity, predictive values, and likelihood ratios of fecal occult blood test for the detection of colorectal cancer in hospital settings" Clinical and Experimental Gastroenterology. Sep. 9, 2015,8:279-284.
Emre, et al. "Clinical Diagnostic Driteria for Dementia Associated with Parkinson's Disease" Movement Disorders. 2007;22(12):1689-1707.
European Patent Office, Communication pursuant to Article 94(3) EPC for EP Application No. 14822061.9 dated Mar. 29, 2018, 7 pp.
European Patent Office, Extended European Search Report for 17816197.2 dated Feb. 19, 2019, 11 pages.
Fan, et al., "Structural and functional biomarkers of prodromal Alzheimer's disease: a high-dimensional pattern classification study," Neuroimage, vol. 41, No. 2, 2008, pp. 227-285.
Gottesman, et al., "The endophenotype concept in psychiatry: etymology and strategic intentions," American Journal of Psychiatry, Apr. 2003; 160(4), pp. 636-645.
Korean Intellectual Property Office, International Search Report and Written Opinion for PCT/ JS2014/046015 dated Oct. 22, 2014, 15 pp.
Jani, et al. "Recommendations for Use and Fit-for-Purpose Validation of Biomarker Multiplex Ligand Binding Assays in Drug Development" AAPS Journal, vol. 18, No. 1, Jan. 2016.
Janocko, et al., "Neuropathologically defined subtypes of Alzheimer's disease differ significantly from neurofibrillary tangle-predominant dementia," Acta Neuropathologica, Nov. 2012, vol. 124(5), pp. 681-692.
Kounnas, et al., "Modulation of g-Secretase Reduces b-Amyloid Deposition in a Transgenic Mouse Model of Alzheimer's Disease," Neuron 67, Sep. 9, 2010, pp. 769-780.
Lee, et al. "The National Mammography Database: Preliminary Data" American Journal of Roentgenology. Apr. 2016; 206(4):883-890.
Lundquist, et al. Screening for Alzheimer's Disease: Inspiration and Ideas from Breast Cancer Strategies. Journal of Applied Gerontology. 2015;34(3):317-328.
Lopponen, et al., "Diagnosing cognitive impairment and dementia in primary health care—a more active approach is needed," Age and Ageing vol. 32:6, Apr. 2003, pp. 606-612.
Nilufer, E-T, "Gene expression endophenotypes: a novel approach for gene discovery in Alzheimer's disease," Molecular Neurodegeneration, 2011, vol. 6:31, 18 pp.
O'Bryant, et al. "Estimating the Predictive Value of the Test of Memory Malingering: An Illustrative Example for Clinicians" Clinical Neuropsychologist. 2006;20(3):533-540.
O'Bryant S.E., et al., "A Blood-Based Algorithm for the Detection of Alzheimer's Disease," Dementia and Geriatric Cognitive Disorders, Aug. 24, 2011, vol. 32, pp. 55-62.
Petersen, et al. "Mild Cognitive Impairment: An Overview" CNS Spectrums. Jan. 2008;13(1):45-53.

(56) References Cited

OTHER PUBLICATIONS

Piper, et al. "Diagnostic and Predictive Accuracy of Blood Pressure Screening Methods with Consideration of Rescreening Intervals: A Systematic Review for the U.S. Preventive Services Task Force" Annals of Internal Medicine. Feb. 2015;162(3):192-204.
Plumb, et al. "Sensitivity and specificity of CT colonography for the detection of colonic neoplasia after positive faecal occult blood testing: Systematic review and meta-analysis" European Radiology. published online Feb. 12, 2014;24( 5):1049-1058.
Reddy, et al., "Identification of Candidate IgG Biomarkers for Alzheimer's Disease via Combinatorial Library Screening," Cell (144), Jan. 7, 2011, pp. 132-142.
Canadian Intellectual Property Office, Examination Report for Canadian Appl. No. 2,920,474 dated Dec. 28, 2017, 4 pp.
European Patent Office, Communication pursuant to Article 94(3) EPC for EP Application No. 148651078.8 dated Jun. 14, 2018, 5 pp.
Akiyama, et al. "Inflammation and Alzheimer's disease" Neurobiol Aging. May-Jun. 2000;21(3):383-421.
Alves, et al. "CSF amyloid-β and tau proteins, and cognitive performance, in early and untreated Parkinson's Disease: The Norwegian ParkWest study" Journal of Neurology, Neurosurgery and Psychiatry. 2010;81 (10):1080-1086.
Anonymous Consensus report of the Working Group on: "Molecular and Biochemical Markers of Alzheimer's Disease". The Ronald and Nancy Reagan Research Institute of the Alzheimer's Association and the National Institute on Aging Working Group [see comment][erratum appears in Neurobiol Aging May-Jun. 1998;19(3):285]. Neurobiology of Aging. 1998;19(2):109-116.
Australian Government, IP Australia, 1st Examination Report for Australian Patent Appl. No. 2014354808 dated Feb. 14, 2017, 5 pp.
Australian Government, IP Australia, 2nd Examination Report for Australian Patent Appl. No. 2014354808 dated Apr. 11, 2017, 4 pp.
Australian Government, IP Australia, 1st Examination Report for Australian Patent Appl. No. 2018201062 dated Jul. 22, 2019, 5 pp.
Barker, et al. Relative frequencies of Alzheimer disease, Lewy body, vascular and frontotemporal dementia, and hippocampal sclerosis in the State of Florida Brain Bank. Alzheimer Dis Assoc Disord, 2002. 16(4): p. 203-12.
Blasko, I. "Ibuprofen diecreases cytokine-indduced amyloid beta production in neuronal cells" Neurobiology of Disease, Dec. 2001, (6) 1094-1101.
Bond, et al. "Screening for cognitive impairment, Alzheimer's disease and other dementias: Opinions of European caregivers, payors, physicians and the general public" Journal of Nutrition, Health and Aging. 2010;14(7):558-562.
Britschgi, et al. "Blood protein signature for the early diagnosis of Alzheimer's disease" Archives of Neurology, 66 (2); 161-165, Feb. 2009.
Brothers, et al. "Are inflammatory profiles the key to personalized Alzheimer's treatment?" Neurodegenerative Disease Management, Aug. 2013, vol. 3, pp. 343-351.
Chatterjee, et al. Comparative analysis of RNA-Seq data from brain and blood samples of Parkinson's disease. Biochem Biophys Res Commun, 2017.
Cho, et al. Selective translational control of the Alzheimer amyloid precursor protein transcript by iron regulatory protein-1. J Biol Chem, 2010. 285(41): p. 31217-32.
Clark, et al. "Diagnostic accuracy of% retention scores on RBANS verbal memory subtests for the diagnosis of Alzheimer's disease and mild cognitive impairment" Archives of Clinical Neuropsychology. 2010;25(4):318-326.
Clarke, et al. "Advances in blood-based protein biomarkers for Alzheimer's disease" Alzheimer's Research and Therapy, 5(3); 18, May 9, 2013.
Ding, et al. Association of SNCA with Parkinson: replication in the Harvard NeuroDiscovery Center Biomarker Study. Mov Disord, 2011. 26(12): p. 2283-6.
Ferman, et al. Inclusion of RBD improves the diagnostic classification of dementia with Lewy bodies. Neurology., 2011. 77(9): p. 875-882.
Ferreti, et al. "Intracellular Aβ-oligomers and early inflammation in a model of Alzheimer's disease" Neurobiology of Aging, vol. 33, Issue 7, Jul. 2012, pp. 1329-1342.
Fiss, et al. Cognitive impairment in primary ambulatory health care: Pharmacotherapy and the use of potentially inappropriate medicine. International Journal of Geriatric Psychiatry. 2013;28(2):173-181.
Fujishiro, et al. Validation of the neuropathologic criteria of the third consortium for dementia with lewy bodies for prospectively diagnosed cases. Journal of Neuropathology and Experimental Neurology, Jul. 2008. 67(7): p. 649-656.
Gerlach, et al. "Biomarker candidates of neurodegeneration in Parkinson's disease for the evaluation of disease-modifying therapeutics" Journal of Neural Transmission, 2012. 119(1): p. 39-52.
Gold, et al. The emergence of diagnostic imaging technologies in breast cancer: Discovery, regulatory approval, reimbursement, and adoption in clinical guidelines. Cancer Imaging, 2012. 12(1): p. 13-24.
Gottesman, et al., Genetic theorizing and schizophrenia. British Journal of Psychiatry. 1973;122(566):15-30.
Graff-Radford, et al. Imaging and acetylcholinesterase inhibitor response in dementia with Lewy bodies. Brain, 2012. 135(8): p. 2470-2477.
Green, et al. "Alterations of p11 in brain tissue and peripheral blood leukocytes in Parkinson's disease" Proc Natl Acad Sci U S A, 2017.
Groveman, et al. Rapid and ultra-sensitive quantitation of disease-associated alpha-synuclein seeds in brain and cerebrospinal fluid by alphaSyn RT-QuIC. Acta Neuropathol Commun, 2018. 6(1): p. 7.
Halliday, et al. Neuropathology underlying clinical variability in patients with synucleinopathies. Acta neuropathologica, 2011. 122(2): p. 187-204.
Hampel, et al. "Precision Medicine: The Golden Gate for detection, treatment and prevention of Alzheimer's disease" Journal of Prevention of Alzheimer's Disease, Dec. 2016 3(4): p. 243-259.
Hansson, et al. Blood-based NfL: A biomarker for differential diagnosis of parkinsonian disorder. Neurology, Mar. 7, 2017. 930-937.
Hely, et al. The Sydney multicenter study of Parkinson's disease: the inevitability of dementia at 20 years. Mov Disord, Apr. 2008. 23(6): p. 837-44.
Henchcliffe, et al. Biomarkers of Parkinson's disease and Dementia with Lewy bodies. Progress in Neurobiology, 2011. 95(4): p. 601-613.
Hennecke, et al. RNA biomarkers of Parkinson's disease: developing tools for novel therapies. Biomark Med, 2008. 2(1): p. 41-53.
Henriksen, et al. "The future of blood-based biomarkers for Alzheimer's disease" Alzheimer's & Dementia, in press, 2013 (Published online Jul. 11, 2013).
Higuchi, et al. "Glucose hypometabolism and neuropathological correlates in brains of dementia with Lewy bodies" Experimental Neurology, 2000. 162(2): p. 247-256.
Ho, et al. "Bridging molecular genetics and biomarkers in Lewy body and related disorders" International Journal of Alzheimer's Disease, 2011.
Hu, et al. Biomarker discovery for Alzheimer's disease, frontotemporal lobar degeneration, and Parkinson's disease. Acta Neuropathologica, 2010. (Published Online Jul. 22, 2010) 120(3): p. 385-399.
Hu, et al. "Transcriptional modulator H2A histone family, member Y (H2AFY) marks Huntington disease activity in man and mouse" Proc Natl Acad Sci U S A, 2011. 108(41): p. 17141-6.
Huse, et al. "Burden of illness in Parkinson's disease" Mov Disord, 2005. 20(11): p. 1449-54.
Kaerst, et al. "Using cerebrospinal fluid marker profiles in clinical diagnosis of dementia with lewy bodies, Parkinson's disease, and Alzheimer's disease" Journal of Alzheimer's Disease, 2014. 38(1): p. 63-73.
Kantarci, et al. Multimodality Imaging Characteristics of Dementia with Lewy bodies. Neurobiology of aging, 2012. 33(9): p. 2091-105.
Kim, et al. "Interactions between pro-inflammatory cytokines and statins on depression in patients with acute coronary syndrome" Prog Neuropsychopharmacol Biol Psychiatry, 2018. 80(Pt C): p. 250-254.

(56) References Cited

OTHER PUBLICATIONS

Kosaka, et al. "Presenile dementia with Alzheimer-, Pick- and Lewy-body changes" Acta neuropathologica, 1976. 36 (3): p. 221-33.
Kuhle, et al. "A highly sensitive electrochemiluminescence immunoassay for the neurofilament heavy chain protein" Journal of Neuroimmunology. 2010;220(1-2):114-119.
Landers, et al. "A High-Intensity Exercise Boot Camp for Persons With Parkinson Disease: A Phase II, Pragmatic, Randomized Clinical Trial of Feasibility, Safety, Signal of Efficacy, and Disease Mechanisms" J Neurol Phys Ther, 2019. 43(1): p. 12-25.
Liu, et al. "Specifically neuropathic Gaucher's mutations accelerate cognitive decline in Parkinson's" Ann Neurol, 2016. 80(5): p. 674-685.
Liu, et al. "Prediction of cognition in Parkinson's disease with a clinical-genetic score: a longitudinal analysis of nine cohorts" Lancet Neurol, 2017. 16(8): p. 620-629.
Lo, et al. "Relationship between patient age and duration of physician visit in ambulatory setting: Does one size fit all?" Journal of the American Geriatrics Society. 2005;53(7):1162-1167.
Locascio, et al. "Association between alpha-synuclein blood transcripts and early, neuroimaging-supported Parkinson's disease" Brain, 2015. 138(Pt 9): p. 2659-71.
Maeck, et al. Dementia diagnostics in primary care: a representative 8-year follow-up study in lower saxony, Germany. Dementia & Geriatric Cognitive Disorders. 2008;25(2):127-134.
McKeith, et al. An evaluation of the predictive validity and inter-rater reliability of clinical diagnostic criteria for senile dementia of Lewy body type. Neurology. 1994;44(5):872-877.
McKeith, et al. Diagnosis and management of dementia with Lewy bodies: Fourth consensus report of the DLB Consortium. Neurology, 2017. 89(1): p. 88-100.
McKeith, et al. Sensitivity and specificity of dopamine transporter imaging with 123I-FP-CIT SPECT in dementia with Lewy bodies: a phase III, multicentre study. Lancet Neurology, 2007. 6(4): p. 305-313.
McKeith, et al. The clinical diagnosis and misdiagnosis of senile dementia of Lewy body type (SDLT). British Journal of Psychiatry 1994; 165(SEP.):324-332.
Mollenhauer, et al. "Serum heart-type fatty acid-binding protein and cerebrospinal fluid tau: marker candidates for dementia with Lewy bodies" Neurodegener Dis, 2007. 4(5): p. 366-75.
Murray, et al. "MRI and pathology of REM sleep behavior disorder in dementia with Lewy bodies" Neurology, 2013. 81(19): p. 1681-9.
Nakamura, et al. High performance plasma amyloid-beta biomarkers for Alzheimer's disease. Nature, 2018. 554 (7691): p. 249-254.
Park, et al. "Differential Diagnosis of Patients with Inconclusive Parkinsonian Features Using [18F]FP-CIT PET/CT" Nuclear Medicine and Molecular Imaging, 2014 (Published Online Dec. 11, 2013) 48(2): p. 106-113.
Piazza, et al. "Increased tissue factor pathway inhibitor and homocysteine in Alzheimer's disease" Neurobiology of Aging. 2010.
Postuma, et al. "MDS clinical diagnostic criteria for Parkinson's disease" Mov Disord, 2015. 30(12): p. 1591-601.
Pykkö, et al. "APOE4 predicts amyloid-β in cortical brain biopsy but not idiopathic normal pressure hydrocephalus" Journal of Neurology, Neurosurgery and Psychiatry. 2012;83(11):1119-1124.
R Development Core Team "R: A language and environment for statistical computing" 2009; www.R-project.org. Version 3.6.0 Apr. 26, 2019.
Scherzer, et al. Molecular markers of early Parkinson's disease based on gene expression in blood. Proc Natl Acad Sci U S A 2007. 104: p. 955-960.
Scherzer, et al. GATA transcription factors directly regulate the Parkinson's disease-linked gene alpha-synuclein. Proc Natl Acad Sci U S A, Aug. 5, 2008. 105(31): p. 10907-12.
Schneider, et al. "Biological marker candidates of alzheimer's disease in blood, plasma, and serum" . CNS Neuroscience and Therapeutics. 2009; 15(4):358-374.
Shaw, et al. "Biomarkers of neurodegeneration for diagnosis and monitoring therapeutics" Nature Reviews. Drug Discovery. Apr. 2007;6(4):295-303.
Sinha, et al. Biomarkers in dementia with Lewy bodies: A review. International Journal of Geriatric Psychiatry, 2012. 27(5): p. 443-453.
Sudduth, et al. "Neuroinflammatory phenotype in early Alzheimer's disease." Neurobiology of Aging, Apr. 2013, vol. 34, pp. 1051-1059.
Szerlip, et al. "Association of cognitive impairment with chronic kidney disease in Mexican Americans" Journal of the American Geriatric Society. 2015;63(10):2023-2028.
Van Blitterswijk, et al. "Anti-superoxide dismutase antibodies are associated with survival in patients with sporadic amyotrophic lateral sclerosis" Amyotroph Lateral Scler, 2011. 12(6): p. 430-8.
Van Den Dungen, et al. "The accuracy of family physicians' dementia diagnoses at different stages of dementia: A systematic review" International Journal of Geriatric Psychiatry 2012;27(4):342-354.
Watson, et al. Screening accuracy for late-life depression in primary care: A systematic review. Journal of Family Practice. Dec. 2003;52(12):956-964.
Wildburger, et al. Amyloid-beta Plaques in Clinical Alzheimer's Disease Brain Incorporate Stable Isotope Tracer In Vivo and Exhibit Nanoscale Heterogeneity. Front Neurol, Mar. 22, 2018. 9: p. 169.
Wright, et al. Geographic and ethnic variation in Parkinson disease: a population-based study of US Medicare beneficiaries. Neuroepidemiology, (published online Jan. 15, 2010) 2010. 34(3): p. 143-51.
Al-Jarrah, et al. Treadmill exercise training could attenuate the upregulation of Interleukin-1beta and tumor necrosis factor alpha in the skeletal muscle of mouse model of chronic/progressive Parkinson disease. NeuroRehabilitation, 2018.
Bauer, et al. "Examining the test of memory malingering trial 1 and word memory test immediate recognition as screening tools for insufficient effort" Assessment. 2007;14(3):215-222.
Canadian Intellectual Property Office, Examination Report for Canadian Appl. No. 2,920,474 dated Jun. 28, 2019, 8 pp.
Canadian Intellectual Property Office, Examination Report for Canadian Appl. No. 3,027,575 dated Apr. 7, 2020, 6 pp.
Colloby, et al. "A comparison of 99mTc-exametazime and 123I-FP-CIT SPECT imaging in the differential diagnosis of Alzheimer's disease and dementia with Lewy bodies" International Psychogeriatrics, 2008. 20(6): p. 1124-1140.
Edwards, et al. Molecular markers of amnestic mild cognitive impairment among Mexican Americans. J Alzheimers Dis, 2016. 49(1): p. 221-8.
Eller, et al. α-Synuclein in Parkinson disease and other neurodegenerative disorders. Clinical Chemistry and Laboratory Medicine, 2011. 49(3): p. 403-408.
European Patent Office, Communication pursuant to Article 94(3) EPC for EP Application No. 148651078.8 dated Oct. 28, 2019, 9 pp.
European Patent Office, Communication pursuant to Article 94(3) EPC for EP Application No. 17816197.2 dated Jan. 9, 2020, 4 pp.
Japan Patent Office, Notification of Reasons for Refusal for Japanese Patent Appl. No. 2017-198118 dated Aug. 22, 2019, with translation. 8 pp.
Japan Patent Office, Notification of Reasons for Refusal for Japanese Patent Appl. No. 2018-566509 dated Jan. 27, 2020, with translation. 9 pp.
McKeith, et al. Operational criteria for senile dementia of Lewy body type (SDLT). Psychological medicine, 1992. 22 (4): p. 911-22.
Shtilbans, et al. "Biomarkers in Parkinson's disease: An update" Current Opinion in Neurology, 2012. 25(4): p. 460-465.
Sverzellati, et al. "Low-dose computed tomography for lung cancer screening: comparison of performance between annual and biennial screen" European Radiology 2016:1-9.
Van Oijen, et al. "Plasma Abeta(1-40) and Abeta(1-42) and the risk of dementia: a prospective case-cohort study" [see comment]. Lancet Neurology. 2006;5(8):655-660.
Villarreal, et al. "Serum-based protein profiles of Alzheimer's disease and mild cognitive impairment in elderly Hispanics" Neurodegener Dis Manag. 2016,6(3), 203-213.

(56) References Cited

OTHER PUBLICATIONS

Villemagne, et al. "Long night's journey into the day: Amyloid-β imaging in Alzheimer's disease" Journal of Alzheimer's Disease. 2013;33(Suppl. 1):S349-S359.
Waring, et al. for the Texas Alzheimer's Research Consortium. "The Texas Alzheimer's Research Consortium longitudinal research cohort: Study design and baseline characteristics" Texas Public Health Journal. 2008,60(3):9-13.
International Search Report and Written Opinion for PCT/US2020/018297 dated Jun. 23, 2020.
Cummings, et al. "Fit-for-purpose biomarker method validation for application in clinical trials of anticancer drugs" British Journal of Cancer, published online Oct. 5, 2010; 103(9):1313-1317.
European Patent Office, Communication pursuant to Article 94(3) EPC for EP Application No. 14822061.9 dated Jan. 7, 2019, 5 pp.
Hakimi, et al. Parkinson's disease-linked LRRK2 is expressed in circulating and tissue immune cells and upregulated following recognition of microbial structures. J Neural Transm, 2011. 118(5): p. 795-808.
Henriksen, "The future of blood-based biomarkers for Alzheimer's disease", Alzheimers Dement, 10(1), 2014, pp. 115-131.
International Search Report and Written Opinion issued in App. No. PCT/US2022/018974, dated Jun. 2, 2022, 21 pages.
Koyama, et al., "The Role of Peripheral Inflammatory Markers in Dementia and Alzheimer's Disease: A Meta-Analysis", J Geronol A Biol Sci Med Sci, vol. 68, No. 4, Apr. 2013, pp. 433-440.
Mueller, et al. "Ways toward an early diagnosis in Alzheimer's disease: The Alzheimer's Disease Neuroimaging Initiative (ADNI)" Alzheimer's and Dementia. 2005;1(1):55-66.
Novak KR, J. "Hispanics/Latinos and Alzheimer's Disease" Alzheimer's Association; May 18, 2004.
O'Bryant S.E., et al., "Biomarkers of Alzheimer's Disease Among Mexican Americans," J. Alzheimers Dis., Dec. 2007, pp. 1-9.
Petersen, Ronald C. "Mild Cognitive Impairment Clinical Trials" Nature, Aug. 2003, vol. 2, pp. 646-653.
Vignini et al., "Alzheimer's Disease and Diabetes: New Insights and Unifying Therapies", Current Diabetes Reviews, 2013, 9, 000-000.
Office Action (Non-Final Rejection) dated Jun. 8, 2023 for U.S. Appl. No. 17/193,907 (pp. 1-20).
Adapt Research Group, et al., "Naproxen and celecoxib do not prevent AD in early results from a randomized controlled trial", Neurology, vol. 68, 2007, pp. 1800-1808.
Aisen, et al., "Effects of Rofecoxib or Naproxen vs Placebo on Alzheimer disease progression: a randomized controlled trial", JAMA, vol. 289, No. 21, Jun. 4, 2003, pp. 2819-2826.
Aisen, et al., "Neither Rofecoxib Nor Naproxen Slows Cognitive Decline In People With Mild-To-Moderate Alzheimer's Disease", Evidence-Based Healthcare, vol. 7, 2003, pp. 200-201.
American Gerontological Society, "The Gerontological Society of American Workgroup on Cognitive Impairment Detection: Report and Recommendations", 2015.
Anthony, et al., "Reduced prevalence of AD in users of NSAIDs and H2 receptor antagonists: the Cache County study", Neurology, vol. 54, 2000, pp. 2066-2071.
Bhavadharini, et al., "Use of capillary blood glucose for screening for gestational diabetes mellitus in resource-constrained settings", Acta Diabetologica, vol. 53(1), 2016, pp. 91-97.
Breitner, et al., "Extended reslts of the Alzheimer disease anti-inflammatory prevention trial (ADAPT)", Alzheimers Dement, vol. 7, No. 4, Jul. 2011, pp. 402-411.
Campari, et al., "Impact of the Introduction of Digital Mammography in an Organized Screening Program on the Recall and Detection Rate", J Digital Imaging, vol. 29(2), 2016, pp. 235-242.
Connell, et al., "Black and white adult family members' attitudes toward a dementia diagnosis", J Amer Geriatrics Soc, vol. 57(9), Sep. 2009, pp. 1562-1568.
Cummings, et al., "Fit-for-purpose biomarker method validation for application in clinical trials of anticancer drugs", British J Cancer, published online Oct. 5, 2010, vol. 103(9), 2010, pp. 1313-1317.

Cunningham, et al., "Oxidative stress, testosterone, and cognition among Caucasian and Mexican American men with and without Alzheimer's disease", J Alzheimers Dis, vol. 40, No. 3, 2014, pp. 563-573.
Duong, et al., "C-reactive Protein-Like Immunoreactivity In The Neurofibrillary Tangles Of Alzheimer's Disease", Brain Res, vol. 749, 1997, pp. 152-156.
Durrenberger, et al., "Common mechanisms in neurodegeneration and neuroinflammation: a BrainNet Europe gene expression microarray study", J Neural Trans, vol. 122, 2015, pp. 1055-1068.
Edwards, et al., "Molecular markers of neuropsychological functioning and Alzheimer's disease", Alzheimer's & Dementia: Diagnosis, Assessment & Disease Monitoring, vol. 1, No. 1, Mar. 1, 2015, pp. 61-66.
Etminan, et al., "Effect of non-steroidal anti-inflammatory drugs on risk of Alzheimer's disease: systematic review and meta-analysis of observational studies", BMJ, vol. 327, Jul. 19, 2003, pp. 128-132.
Fillit, et al., "Economics of dementia and pharmacoeconomics of dementia therapy", Am J Geriatric Pharmacotherapy, vol. 3(1), Mar. 2005, pp. 39-49.
Gasparini, et al., "Non-steroidal anti-inflammatory drugs (NSAIDs) in Alzheimer's disease: old and new mechanisms of action", J Neurochem, vol. 91, 2004, pp. 521-536.
Gotschall, P.E., "β-amyloid induction of gelatinase B secretion in cultured microglia: inhibition by dexamethasone and indomethacin", NeuroReport, vol. 7, No. 18, 1996, pp. 3077-3080.
Grundman, et al., "Treatment of Alzheimer's Disease: Rationale and Strategies", Neurologic Clinics, vol. 18, 2000, pp. 807-827.
Hall, et al., "The impact of APOE status on relationship of biomarkers of vascular risk and systemic inflammation to neuropsychiatric symptoms in Alzheimer's disease", J Alzheimer's Dis, vol. 40, 2014, pp. 887-896.
Harvey, et al., "A systematic review of the diagnostic accuracy of prostate specific antigen", BMC Urology, vol. 9(1), Sep. 10, 2009.
Heneka, et al., "Innate immune activation in neurodegenerative disease", Nat Rev Immunol, vol. 14, 2014, pp. 463-477.
Hirohata, et al., "Non-steroidal anti-inflammatory drugs have anti-amyloidogenic effects for Alzheimer's β-amyloid fibrils in vitro", Neuropharmacol, vol. 49, 2005, pp. 1088-1099.
Hurd, et al., "Monetary Costs of Dementia in the United States", N Engl J Med, vol. 368, No. 14, Apr. 14, 2013, pp. 1326-1334.
In't Veld, B.A., et al., "Nonsteroidal Antiinflammatory Drugs and the Risk of Alzheier's Diesease", N Engl J Med, vol. 345, No. 21, 2001, pp. 1515-1521.
Iwamoto, et al., "Demonstration of CRP immunoreactivity in brains of Alzheimer's disease: immunohistochemical study using formic acid pretreatment of tissue sections", Neurosci Lett, vol. 177, 1994, pp. 23-26.
Johnson, et al., "A depressive endophenotype of poorer cognition among cognitively healthy community-dwelling adults: Results from the Western Australia Memory Study", Intl J Geriatr Psychiatry, vol. 30, No. 8, 2015, pp. 881-886.
Klegeris, et al., "Non-steroidal anti-inflammatory drugs (NSAIDs) and other anti-inflammatory agents in the treatment of neurodegenerative disease", Curr Alzheimer Res, vol. 2, 2005, pp. 355-365.
Knopman, et al., "Patterns of Care in the Early Stages of Alzheimer's Disease: Impediments to Timely Diagnosis", J Am Geriatrics Soc, vol. 48(3), 2000, pp. 300-304.
Lee, et al., "Fit-for-purpose Method Development and Validation for Successful Biomarker Measurement", Pharmaceutical Res, vol. 23(2), 2006, pp. 312-328.
Lyketsos, et al., "Developing new treatments for Alzheimer's disease: The who, what, when, and how of biomarker-guided therapies", Int Psychogeriatr, vol. 20, No. 5, 2008, pp. 871-889.
Mackenzie, et al., "Nonsteroidal anti-inflammatory drugs use and Alzheimer-type pathology in aging", Neurology, vol. 50, 1998, pp. 986-990.
Mcgeer, et al., "The importance of inflammatory mechanisms in Alzheimer disease", Exp Gerontol, vol. 33, No. 5, 1998, pp. 371-378.
Mueller, et al., "Ways toward an early diagnosis in Alzheimer's disease: The Alzheimer's Disease Neuroimaging Initiative (ADNI)", Alzheimer's and Dementia, vol. 1(1), 2005, pp. 55-66.

(56) References Cited

OTHER PUBLICATIONS

Netland, et al., "Indomethacin reverses the microglial response to amyloid β-protein", Neurobiol Aging, vol. 19, No. 3, 1998, pp. 201-204.

Novak, et al., "Hispanics/Latinos and Alzheimer's Disease", Alzheimer's Association, May 18, 2004, pp. 1-8.

O'Bryant, et al., "A blood screening test for Alzheimer's disease", Alzheimer's & Dementia: Diagnosis, Assessment & Disease Monitoring, vol. 3, Jun. 25, 2016, pp. 83-90.

O'Bryant, et al., "A Proinflammatory Endophenotype Predicts Treatment Response in a Multicenter Trial of NSAIDS in AD", Alzheimer's & Dementia: The Journal of the Alzheimer's Association, vol. 10, No. 4, supplement, 2014, P273-P274.

O'Bryant, et al., "Risk factors for mild cognitive impairment among Mexican Americans", Alzheimers Dement, vol. 9, No. 6, 2013, pp. 622-631.

O'Bryant, et al., "Texas Research and Care Consortium. The Link between C-reactive protein and Alzheimer's disease among Meixcan Americans", J Alzheimers Dis, vol. 34, No. 7, Jan. 1, 2013, pp. 701-706.

Pasinetti, et al., "Clycooxygenase-2 expression is increased in frontal cortex of Alzheimer's disease brain", Neuroscience, vol. 87, No. 2, 1998, pp. 319-324.

Petersen, R.C., "Mild Cognitive Impairment Clinical Trials", Nature, vol. 2, Aug. 2003, pp. 646-653.

Rogers, et al., "Clinical trial of indomethacin in Alzheimer's disease", Neurology, vol. 43, 1993, pp. 1609-1611.

Schmidt, et al., "Early inflammation and dementia: a 25-year follow-up of the Honolulu-Asia Aging Study", Ann Neurol, vol. 52, 2002, pp. 168-174.

Thal, et al., "A Randomized, Double-Blind, Study of Rofecoxib in Patients with Mild Cognitive Impairment", Neuropsychopharmacology, vol. 30, 2005, pp. 1204-1215.

Tocco, et al., "Maturational regulation and regional induction of cyclooxygenase-2 in rat brain: implications for Alzheimer's disease", Exp Neurol, vol. 144, Article No. EN976429, 1997, pp. 339-349.

* cited by examiner

PERSONALIZED MEDICINE APPROACH FOR TREATING COGNITIVE LOSS

CROSS-REFERENCE TO RELATED APPLICATIONS

This application claims priority to, and is the National Phase of International Application No. PCT/US2014/067562, filed on Nov. 26, 2014, which claims the benefit under 35 U.S.C. § 119(e) of U.S. Provisional Application No. 61/908,812, filed Nov. 26, 2013. All of which are hereby incorporated by reference in their entirety.

STATEMENT OF FEDERALLY FUNDED RESEARCH

This invention was made with U.S. Government support by the National Institutes of Health under Grant Number AG039389. The government has certain rights in this invention.

TECHNICAL FIELD OF THE INVENTION

The present invention relates in general to the field of personalized medicine, and more particularly, to a novel method and apparatus for selecting a therapy to improve cognitive function.

INCORPORATION-BY-REFERENCE OF MATERIALS FILED ON COMPACT DISC

None.

BACKGROUND OF THE INVENTION

Without limiting the scope of the invention, its background is described in connection with the treatment of cognitive dysfunctions.

The detection and evaluation of disease conditions has progressed greatly as a result of the sequencing of the human genome and the availability of bioinformatics tools. One such system is taught in U.S. Pat. No. 8,430,816, issued to Avinash, et al., for a system and method for analysis of multiple diseases and severities. Briefly, these inventors teach a data processing technique that includes a computer-implemented method for accessing reference deviation maps for a plurality of disease types. The reference deviation maps may include subsets of maps associated with severity levels of respective disease types and a disease severity score may be associated with each severity level. The method is said to also include selecting patient severity levels for multiple disease types based on the subsets of reference deviation maps. Also, the method may include automatically calculating a combined patient disease severity score based at least in part on the disease severity scores associated with the selected patient severity levels, and may include outputting a report based at least in part on the combined patient disease severity score.

Another such invention, is taught in U.S. Pat. No. 8,008,025, issued to Zhang and directed to biomarkers for neurodegenerative disorders. Briefly, this inventor teaches methods for diagnosing neurodegenerative disease, such as Alzheimer's Disease, Parkinson's Disease, and dementia with Lewy body disease by detecting a pattern of gene product expression in a cerebrospinal fluid sample and comparing the pattern of gene product expression from the sample to a library of gene product expression pattern known to be indicative of the presence or absence of a neurodegenerative disease. The methods are also said to provide for monitoring neurodegenerative disease progression and assessing the effects of therapeutic treatment. Also provided are kits, systems and devices for practicing the subject methods.

United States Patent Application Publication No. 2013/0012403, filed by Hu is directed to compositions and methods for identifying autism spectrum disorders. This application is directed to microRNA chips having a plurality of different oligonucleotides with specificity for genes associated with autism spectrum disorders. The invention is said to provide methods of identifying microRNA profiles for neurological and psychiatric conditions including autism spectrum disorders, methods of treating such conditions, and methods of identifying therapeutics for the treatment of such neurological and psychiatric conditions.

Yet another application is United States Patent Application Publication No. 2011/0159527, filed by Schlossmacher, et al., for methods and kits for diagnosing neurodegenerative disease. Briefly, the application is said to teach methods and diagnostic kits for determining whether a subject may develop or be diagnosed with a neurodegenerative disease. The method is said to include quantitating the amount of alpha-synuclein and total protein in a cerebrospinal fluid (CSF) sample obtained from the subject and calculating a ratio of alpha-synuclein to total protein content; comparing the ratio of alpha-synuclein to total protein content in the CSF sample with the alpha-synuclein to total protein content ratio in CSF samples obtained from healthy neurodegenerative disease-free subjects; and determining from the comparison whether the subject has a likelihood to develop neurodegenerative disease or making a diagnosis of neurodegenerative disease in a subject. It is said that a difference in the ratio of alpha-synuclein to total protein content indicates that the subject has a likelihood of developing a neurodegenerative disease or has developed a neurodegenerative disease.

SUMMARY OF THE INVENTION

In one embodiment, the present invention includes a method for selecting a therapy for improved cognition or prevention of cognitive loss using one or more anti-inflammatory therapies comprising: obtaining a sample from a subject; measuring one or more biomarkers in the sample selected from at least one of interleukin (IL)-7, tumor necrosis factor-alpha (TNFα), IL-5, IL-6, C-reactive protein (CRP), IL-10, tenascin C (TNC), intracellular adhesion molecule-1 (ICAM1), coagulation factor VII (FVII), I309, tumor necrosis factor receptor-1 (TNFR1), alpha-2 macroglobulin (A2M), chemokine (C-C motif) ligand 17 (TARC), eotaxin3, vascular cell adhesion molecule-1 (VCAM1), thrombopoietin (TPO), fatty acid binding protein (FABP), IL-18, beta-2 microblogulin (B2M), serum amyloid A1 cluster (SAA), pancreatic polypeptide (PPY), Parkinson protein 7 (DJ1), beta amyloid (Aβ), tau, or α-synuclein; comparing the level of the one or more biomarkers within a sample of patients suffering from cognitive loss; dividing the level of expression of the one or more markers as being either high proinflammatory or low proinflammatory; and selecting a course of treatment for the subject based on whether the subject is selected as being high proinflammatory or low proinflammatory. In one aspect, the method further comprises the steps of: generating a high and a low proinflammatory endophenotype by determining the level of expression of two or more markers selected from IL7, TNFα, IL5, IL6, CRP, IL10, TNC, ICAM1, FVII, I309, TNFR1, A2M, TARC, eotaxin3, VCAM1, TPO, FABP, IL18, B2M, SAA, PPY, DJ1, Aβ, tau, or α-synuclein; and determining the high and low proinflammatory groupings by determining the level of expression of the two or more biomarkers. In another aspect, the proinflammatory profile is generated using learning machines (random forest, support vector machines), clustering algorithms (factor analysis, principal component analysis), summation of values, or other methods to generate a proinflammatory score across multiple measures. In another aspect, the high end of the score across multiple markers is reflective of the high proinflammatory endophenotype and the low end as the low proinflammatory endophenotype with all others falling in a middle endophenotype. In another aspect, if the subject is scored in the high proinflammatory group an anti-inflammatory treatment is indicated, and if the subject is scored in a low proinflammatory group then an anti-inflammatory treatment is contraindicated. In another aspect, at least one of the biomarker measurements is obtained by a method selected from the group consisting of immunoassay and enzymatic activity assay. In another aspect, the sample is serum or plasma. In another aspect, the cognitive dysfunction is a disease or condition selected from Alzheimer's Disease, Parkinson's Disease, Down's syndrome, Frontotemporal dementia, Dementia with Lewy Bodies, Multiple sclerosis, traumatic brain injury, depression, schizophrenia, bipolar disease (and other mental illness), diabetes, hypertension, stroke, heart attack, dyslipidemia, other conditions/diseases or aging. In another aspect, cognition is "normal" but patients are deemed "at risk" based on their pro-inflammatory endophenotype. In another aspect, the level of expression of the various proteins is measured by at least one of fluorescence detection, chemiluminescence detection, electrochemiluminescence detection and patterned arrays, reverse transcriptase-polymerase chain reaction, antibody binding, fluorescence activated sorting, detectable bead sorting, antibody arrays, microarrays, enzymatic arrays, receptor binding arrays, allele specific primer extension, target specific primer extension, solid-phase binding arrays, liquid phase binding arrays, fluorescent resonance transfer, or radioactive labeling. In another aspect, the high and low end of the proinflammatory group is determined by specifically determining the level of expression of C-reactive protein (CRP) and tumor necrosis factor alpha (TNFα). In another aspect, the high and low end of the proinflammatory group is determined from 2, 3, 4, 5, 6, 7, 8, 9, 10, 11, 12, 13, 14, 15, 16, 17, 18, 19, 20, 21, 22, 23, 24, or 25 biomarkers. In another aspect, the proinflammatory endophenotypes may be treated with one of more of the following non-limiting examples of therapeutic agents: NSAIDs, non-selective NSAIDs, selective NSAIDs, steroids, glucocorticoids, Immune Selective Anti-Inflammatory Derivatives (ImSAIDs), anti-TNF medications, anti-IL5 drugs, or CRP-lowering agents. In another aspect, the one or more of the following therapeutic agents: NSAIDs, non-selective NSAIDs, selective NSAIDs, steroids, glucocorticoids, Immune Selective Anti-Inflammatory Derivatives (ImSAIDs), anti-TNF medications, anti-IL5 drugs or CRP-lowering agents; are contraindicated if the subject does not have a proinflammatory endophenotype. In another aspect, the method further comprises the step of generating a dataset that comprises the level of the one or more biomarkers prior to the step of comparing the level of the one or more biomarkers within a sample of patients suffering from cognitive loss.

In another embodiment, the present invention includes a method for selecting patient therapy for improved cognition comprising: obtaining a sample from a subject; measuring the level of expression of TNFα and CRP in the sample; determining the tertile of the level of expression of the these two biomarkers; and depending on the level of expression dividing the level of expression of the two or more markers as being either high proinflammatory or low proinflammatory; and selecting a course of treatment for the subject based on whether the subject is selected as being high proinflammatory or low proinflammatory, wherein the tertile is determined by: scoring the tertile scores for both markers to generate a score with a range from two to six, assigning a lower score (i.e., 2) to the low end of a proinflammatory, assigning a highest score (i.e., 6) score was assigned to a high end of the proinflammatory, with all other scores falling in a middle score. In another aspect, the method further comprises the step of generating a dataset that comprises the level of expression of TNFα and CRP in the sample prior to the step of determining the tertile of the level of expression of the these two biomarkers; and depending on the level of expression dividing the level of expression of the two or more markers as being either high proinflammatory or low proinflammatory.

In another embodiment, the present invention includes a method for selecting patient therapy for prevention of cognitive loss comprising: obtaining a sample from a subject; measuring the level of expression of TNFα and CRP; determining the tertile of the level of expression of the these two biomarkers; and depending on the level of expression dividing the level of expression of the two or more markers as being either high proinflammatory or low proinflammatory; and selecting a course of treatment for the subject based on whether the subject is selected as being high proinflammatory or low proinflammatory, wherein the tertile is determined by: scoring the tertile scores for both markers to generate a score with a range from two to six, assigning a lower score (i.e., 2) to the low end of a proinflammatory, assigning a highest score (i.e., 6) score was assigned to a high end of the proinflammatory, with all other scores falling in a middle score. In another aspect, if the subject is scored in the tertile that is scored as a high proinflammatory an anti-inflammatory treatment is indicated, and if the subject is scored in a low proinflammatory then an anti-inflammatory treatment is contraindicated. In another aspect, the sample is serum or plasma. In another aspect, the cognitive dysfunction is a disease or condition selected from Alzheimer's Disease, Parkinson's Disease, Down's syndrome, Frontotemporal dementia, Dementia with Lewy Bodies, Multiple sclerosis, traumatic brain injury, depression, schizophrenia, bipolar disease (and other mental illness), diabetes, hypertension, stroke, heart attack, dyslipidemia, other conditions/diseases or aging. In another aspect, the level of expression of the various proteins is measured by at least one of fluorescence detection, chemiluminescence detection, electrochemiluminescence detection and patterned arrays, reverse transcriptase-polymerase chain reaction, antibody binding, fluorescence activated sorting, detectable bead sorting, antibody arrays, microarrays, enzymatic arrays, receptor binding arrays, allele specific primer extension, target specific primer extension, solid-phase binding arrays, liquid phase binding arrays, fluorescent resonance transfer, or radioactive labeling.

In another embodiment, the present invention includes a method determining the effectiveness of a candidate drug that impacts the inflammatory system to evaluate the candidate drug believed to be useful in treating a cognitive loss, the method comprising: (a) measuring one or more biomarkers in a sample of serum or plasma obtained from a subject suspected of having cognitive loss selected from IL7, TNFα, IL5, IL6, CRP, IL10, TNC, ICAM1, FVII, I309, TNFR1, A2M, TARC, eotaxin3, VCAM1, TPO, FABP, IL18, B2M, SAA, PPY, DJ1, Aβ, tau, or α-synuclein; (b) administering the candidate drug to a first subset of the patients, and a placebo to a second subset of the patients; (c) generating a proinflammatory group dataset using one or a combination of the one or more biomarkers; (d) determining the tertile of the level of expression of the one or more biomarkers; and depending on the level of expression dividing the level of expression of the one or more biomarkers as being either high proinflammatory or low proinflammatory; (e) determining if a baseline proinflammatory group predicted treatment response such that the high proinflammatory group responded differentially than the low proinflammatory group; (f) repeating step (a) after the administration of the candidate drug or the placebo; (g) determining if the candidate drug modifies the proinflammatory profile over the course of the trial; and (h) determining if change in the proinflammatory profile over the course of the trial predicted a positive response, a negative response, or a no treatment response, and if a statistically significant treatment response for cognitive loss, cognitive improvement or stability of cognitive functioning with the candidate drug is obtained, wherein a change in the proinflammatory profile is indicative of the candidate drug having effectiveness. In one aspect, the method further comprises the steps of obtaining one or more additional blood samples from the patient after a pre-determined amount of time and comparing the levels of the biomarkers from the one or more additional samples to determine progression of cognitive loss. In another aspect, the method further comprises the steps of treating the patient for a pre-determined period of time, obtaining one or more additional blood samples from the patient after the pre-determined amount of time and comparing the levels of the biomarkers from the one or more additional samples to determine progression of cognitive loss.

In another embodiment, the present invention includes a method of determining the effectiveness of a candidate drug that impacts the inflammatory system to evaluate the candidate drug believed to be useful in preventing cognitive loss, the method comprising: (a) measuring one or more biomarkers in a sample of serum or plasma obtained from a subject suspected of having cognitive loss selected from IL7, TNFα, IL5, IL6, CRP, IL10, TNC, ICAM1, FVII, I309, TNFR1, A2M, TARC, eotaxin3, VCAM1, TPO, FABP, IL18, B2M, SAA, PPY, DJ1, Aβ, tau, or α-synuclein; (b) administering the candidate drug to a first subset of the patients, and a placebo to a second subset of the patients; (c) generating the proinflammatory groups using one or a combination of the one or more biomarkers; (d) determining the tertile of the level of expression of the one or more biomarkers; and depending on the level of expression dividing the level of expression of the one or more markers as being either high proinflammatory or low proinflammatory; (e) determining if baseline proinflammatory group predicted treatment response such that the high proinflammatory group responded differentially than the low proinflammatory group; (f) repeating step (a) after the administration of the candidate drug or the placebo; (g) determining if the candidate drug modifies the proinflammatory profile over the course of the trial; and (h) determining if change in the proinflammatory profile over the course of the trial predicted a positive response, a negative response, or a no treatment response, and if a statistically significant treatment response for cognitive loss, cognitive improvement or stability of cognitive functioning with the candidate drug is obtained, wherein a change in the metabolic profile is indicative of the candidate drug having effectiveness. In one aspect, the method further comprises the steps of obtaining one or more additional blood samples from the patient after a pre-determined amount of time and comparing the levels of the biomarkers from the one or more additional samples to determine progression of cognitive loss. In another aspect, the method further comprises the steps of treating the patient for a pre-determined period of time, obtaining one or more additional blood samples from the patient after the pre-determined amount of time and comparing the levels of the biomarkers from the one or more additional samples to determine progression of cognitive loss.

In another embodiment, the present invention includes a method determining the effectiveness of a candidate drug that impacts the inflammatory system to evaluate the candidate drug believed to be useful in preventing or treating a cognitive loss, the method comprising: (a) measuring the serum or plasma based levels of CRP and TNFα; (b) administering the candidate drug to a first subset of the patients, and a placebo to a second subset of the patients; (c) generating the proinflammatory groups using a combination of CRP and TNFα for the first and second subset of patients; (d) determining the tertile of the level of expression of CRP and TNFα in the first and second subset of patients; (e) dividing the level of expression of CRP and TNFα as being either high proinflammatory or low proinflammatory depending on the level of expression of CRP and TNFα; (f) determining if baseline proinflammatory group predicted treatment response such that the high proinflammatory group responded differentially than the low proinflammatory group, (g) repeating step (a) after the administration of the candidate drug or the placebo; and (h) determining if the candidate drug modifies the proinflammatory profile over the course of the trial. In one aspect, the method further comprises the step of determining if change in the proinflammatory profile based on CRP and TNFα over the course of the trial predicted both positive and negative treatment response as well as no treatment response and if a statistically significant treatment response for the candidate drug was achieved as a primary or secondary outcome of the clinical trial. In another aspect, the method further comprises the steps of obtaining one or more additional blood samples from the patient after a pre-determined amount of time and comparing the levels of CRP and TNFα from the one or more additional samples to determine progression of cognitive loss. In another aspect, the method further comprises the steps of: treating the patient for a pre-determined period of time, obtaining one or more additional blood samples from the patient after the pre-determined amount of time and comparing the levels of the biomarkers from the one or more additional samples to determine progression of cognitive loss.

In another embodiment, the present invention includes a method for selecting a therapy for improved cognition using one or more anti-diabetic therapies comprising: obtaining a sample from a subject; measuring one or more biomarkers in the sample selected from alpha-2-macroglobulin (A2M), fatty acid binding protein (FABP), pancreatic polypeptide (PPP), glucagon like peptide 1 (GLP-1), peptide YY (PYY), insulin, glycated hemoglobin A1c (HbA1c), glucose, triglycerides, high density lipoprotein (HDL), low density lipoproteins (LDL and vLDLs), diacylglycerol acyl-transferase 1 (DGAT1), peroxisome proliferator-activated receptor (PPAR)-γ, PPARα, cholesterol, body mass index (BMI), or waist circumference; comparing the level of the one or more biomarkers within a sample of patients suffering from cognitive loss; dividing the level of expression of the one or more markers as being either high metabolic dysfunction endophenotype or low metabolic dysfunction endophenotype; and selecting a course of treatment for the subject based on whether the subject is selected as being high metabolic dysfunction endophenotype or low metabolic dysfunction endophenotype, wherein a high metabolic endophenotype subject benefits from a treatment with an anti-diabetic drug. In another aspect, the method further comprises the steps of: generating a high and a low metabolic endophenotype by determining the level of expression of two or more biomarkers selected from alpha-2-macroglobulin (A2M), fatty acid binding protein (FABP), pancreatic polypeptide (PPP), glucagon like peptide 1 (GLP-1), peptide YY (PYY), insulin, glycated hemoglobin A1c (HbA1c), glucose, triglycerides, high density lipoprotein (HDL), low density lipoproteins (LDL and vLDLs), diacylglycerol acyltransferase 1 (DGAT1), peroxisome proliferator-activated receptor (PPAR)-γ, PPARα, cholesterol, body mass index (BMI), or waist circumference; and determining the high and low metabolic groupings by determining the level of expression of the two or more biomarkers. In one aspect, the metabolic profile is generated using learning machines (random forest, support vector machines), clustering algorithms (factor analysis, principal component analysis), summation of values, or other methods to generate a metabolic score across multiple measures. In another aspect, the high end of the score across multiple markers is reflective of the high metabolic dysfunction endophenotype and the low end as the low metabolic dysfunction endophenotype with all others falling in a middle endophenotype. In another aspect, if the subject is scored in the high metabolic dysfunction group an anti-diabetic treatment is indicated, and if the subject is scored in a low metabolic dysfunction group then an anti-diabetic treatment is contraindicated. In another aspect, at least one of the biomarker measurements is obtained by a method selected from the group consisting of immunoassay and enzymatic activity assay. In another aspect, the sample is serum or plasma.

In another aspect, the cognitive dysfunction is a disease or condition selected from Alzheimer's Disease, Parkinson's Disease, Down's syndrome, Frontotemporal dementia, Dementia with Lewy Bodies, Multiple sclerosis, traumatic brain injury, depression, schizophrenia, bipolar disease (and other mental illness), diabetes, hypertension, stroke, heart attack, dyslipidemia, other conditions/diseases or aging. In another aspect, cognition is "normal" but patients are deemed "at risk" based on their metabolic endophenotype. In another aspect, the level of expression of the various proteins is measured by at least one of fluorescence detection, chemiluminescence detection, electrochemiluminescence detection and patterned arrays, reverse transcriptase-polymerase chain reaction, antibody binding, fluorescence activated sorting, detectable bead sorting, antibody arrays, microarrays, enzymatic arrays, receptor binding arrays, allele specific primer extension, target specific primer extension, solid-phase binding arrays, liquid phase binding arrays, fluorescent resonance transfer, or radioactive labeling. In another aspect, the high and low end of the metabolic group is determined by specifically determining the level of expression of FABP and PPP. In another aspect, the high and low end of the metabolic group is determined from 2, 3, 4, 5, 6, 7, 8, 9, 10, 11, 12, 13, 14, 15, 16, 17, 18 or 19 biomarkers. In another aspect, the metabolic endophenotype may be treated with one of more of the following non-limiting examples of therapeutic agents: with anti-diabetic, insulin, GLP-1 medications would be utilized for those whose metabolic endophenotype weighs GLP-1, Amylin-related medications, or oral hypoglycemics.

In another embodiment, the present invention includes a method for selecting patient therapy for improved cognition or prevention of cognitive loss comprising: obtaining a sample from a subject; measuring the level of expression of two or more biomarkers selected from FABP and PPP; determining the tertile of the level of expression of the two or more biomarkers; and depending on the level of expression dividing the level of expression of the two or more markers as being either high metabolic or low metabolic; and selecting a course of treatment for the subject based on whether the subject is selected as being high metabolic endophenotype or low metabolic endophenotype, wherein the tertile is determined by: scoring the tertile scores for both markers to generate a score with a range from two to six, assigning a lower score (i.e., 2) to the low end of a metabolic, assigning a highest score (i.e., 6) score was assigned to a high end of the metabolic, with all other scores falling in a middle score. In one aspect, if the subject is scored in the tertile that is scored as a high metabolic an anti-diabetic treatment is indicated, and if the subject is scored in a low metabolic then an anti-diabetic treatment is contraindicated. In another aspect, the sample is serum or plasma. In another aspect, the cognitive dysfunction is a disease or condition selected from Alzheimer's Disease, Parkinson's Disease, Down's syndrome, Frontotemporal dementia, Dementia with Lewy Bodies, Multiple sclerosis, traumatic brain injury, depression, schizophrenia, bipolar disease (and other mental illness), diabetes, hypertension, stroke, heart attack, dyslipidemia, other conditions/diseases or aging. In another aspect, cognition is "normal" but patients are deemed "at risk" based on their proinflammatory endophenotype. In another aspect, the level of expression of the various proteins is measured by at least one of fluorescence detection, chemiluminescence detection, electrochemiluminescence detection and patterned arrays, reverse transcriptase-polymerase chain reaction, antibody binding, fluorescence activated sorting, detectable bead sorting, antibody arrays, microarrays, enzymatic arrays, receptor binding arrays, allele specific primer extension, target specific primer extension, solid-phase binding arrays, liquid phase binding arrays, fluorescent resonance transfer, or radioactive labeling. In another aspect, the method further comprises the step of generating a dataset that comprises expression data from the two or more biomarkers prior to the step of generating a high and a low metabolic endophenotype by determining the level of expression of two or more markers.

In another embodiment, the present invention includes a method of determining the effectiveness of a candidate drug that impacts the metabolism to evaluate the candidate drug believed to be useful in treating and/or preventing cognitive loss, the method comprising: (a) measuring one or more biomarkers in a sample of serum or plasma obtained from a subject suspected of having cognitive loss selected from A2M, fatty acid binding protein (FABP), pancreatic polypeptide (PPP), glucagon like peptide 1 (GLP-1), peptide YY (PYY), insulin, HbA1c, glucose, triglycerides, HDL, LDL, vLDL, DGAT1, PPAR-γ, PPARα, cholesterol, BMI, waist circumference; (b) administering the candidate drug to a first subset of the patients, and a placebo to a second subset of the patients; (c) generating the metabolic groups using one or a combination of the one or more biomarkers; (d) determining the tertile of the level of expression of the one or more biomarkers; and depending on the level of expression dividing the level of expression of the one or more markers as being either high metabolic dysfunction or low metabolic dysfunction; (e) determining if baseline metabolic group predicted treatment response such that the high metabolic group responded differentially than the low metabolic dysfunction group; (f) repeating step (a) after the administration of the candidate drug or the placebo; (g) determining if the candidate drug modifies the metabolic profile over the course of the trial; and (h) determining if change in the metabolic profile over the course of the trial predicted a positive response, a negative response, or a no treatment response, and if a statistically significant treatment response with the candidate drug is obtained. In another aspect, the method further comprises the steps of obtaining one or more additional blood samples from the patient after a pre-determined amount of time and comparing the levels of the biomarkers from the one or more additional samples to determine progression of cognitive loss. In another aspect, the method further comprises the steps of treating the patient for a pre-determined period of time, obtaining one or more additional blood samples from the patient after the pre-determined amount of time and comparing the levels of the biomarkers from the one or more additional samples to determine progression of cognitive loss.

In another embodiment, the present invention includes a method of determining the effectiveness of a candidate drug that impacts metabolism to evaluate the candidate drug believed to be useful in treating or preventing cognitive loss, the method comprising: (a) measuring the serum or plasma based levels of two or more markers selected from fatty acid binding protein, CD40, glucagon like protein-1 (GLP-1), IgM, β-2 microglobulin, IGF-binding protein 2, IL-8, peptide YY, macrophage derived chemokine (MDC), macrophage inflammatory protein-1 (MIP-1 alpha), pancreatic polypeptide, vLDL, DGAT1, PPAR-γ, PPARα; (b) administering a candidate drug to a first subset of the patients, and a placebo to a second subset of the patients; (c) generating the metabolic groups using a combination of the two or more biomarkers for the first and second subset of patients; (d) determining the tertile of the level of expression of the two or more biomarkers in the first and second subset of patients; (e) dividing the level of expression of the two or more biomarkers as being either high metabolic or low metabolic depending on the level of expression of the two or more biomarkers; (f) determining if baseline metabolic group predicted treatment response such that the high metabolic group responded differentially than the low metabolic group, (g) repeating step (a) after the administration of the candidate drug or the placebo; and (h) determining if the candidate drug modifies the metabolism profile over the course of the trial. In one aspect, the method further comprises the step of determining if change in the metabolic profile based on the two or more biomarkers over the course of the trial predicted both positive and negative treatment response as well as no treatment response and if a statistically significant treatment response for the candidate drug was achieved as a primary or secondary outcome of the clinical trial. In one aspect, the method further comprises the steps of obtaining one or more additional blood samples from the patient after a pre-determined amount of time and comparing the levels of FABP and PPP from the one or more additional samples to determine progression of cognitive loss. In another aspect, the method further comprises the steps of: treating the patient for a pre-determined period of time, obtaining one or more additional blood samples from the patient after the pre-determined amount of time and comparing the levels of the biomarkers from the one or more additional samples to determine progression of cognitive loss.

In another embodiment, the present invention includes a method for selecting a therapy for improved cognition or prevention of cognitive loss using one or more anti-diabetic therapies for subjects of Mexican-American ethnogenicity comprising: obtaining a sample from a Mexican-American subject; generating a high and a low metabolic endophenotype by determining the level of expression of two or more markers selected from fatty acid binding protein (FABP), CD40, glucagon like protein-1 (GLP-1), IgM, β-2 microglobulin, IGF-binding protein 2, IL-8, peptide YY, macrophage derived chemokine (MDC), macrophage inflammatory protein-1 (MIP-1 alpha), pancreatic polypeptide, glycated hemoglobin A1c (HbA1c), glucose, triglycerides, high density lipoprotein (HDL), low density lipoproteins (LDL and vLDL), DGAT1, PPAR-γ, PPARα, cholesterol, body mass index (BMI), or waist circumference; comparing the level of the one or more biomarkers within a sample of patients suffering from cognitive loss; dividing the level of expression of the one or more markers as being either high metabolic or low metabolic; and selecting a course of treatment for the subject based on whether the subject is selected as being high metabolic or low metabolic, wherein a high metabolic subject benefits from a treatment with an anti-diabetic drug.

In another embodiment, the present invention includes a method of conducting a clinical trial of a drug that impacts metabolism of subjects of Mexican-American ethnogenetics to evaluate the candidate drug believed to be useful in treating and/or preventing cognitive loss, the method comprising: (a) measuring the serum or plasma based levels of two or more markers selected from two or more markers selected from fatty acid binding protein (FABP), CD40, glucagon like protein-1 (GLP-1), IgM, β-2 microglobulin, IGF-binding protein 2, IL-8, peptide YY, macrophage derived chemokine (MDC), macrophage inflammatory protein-1 (MIP-1 alpha), pancreatic polypeptide, and one or more physiological markers selected from glycated hemoglobin A1c (HbA1c), glucose, triglycerides, high density lipoprotein (HDL), low density lipoproteins (LDL, vLDL), DGAT1, PPAR-γ, PPARα, cholesterol, body mass index (BMI), or waist circumference; (b) administering a candidate drug to a first subset of the patients, and a placebo to a second subset of the patients; (c) generating the metabolic groups using a combination of the two or more biomarkers for the first and second subset of patients; (d) determining the tertile of the level of expression of the two or more biomarkers in the first and second subset of patients; (e) dividing the level of expression of the two or more biomarkers as being either high metabolic or low metabolic depending on the level of expression of the two or more biomarkers; and (f) determining if baseline metabolic group predicted treatment response such that the high metabolic group responded differentially than the low metabolic group, (g) repeating step (a) after the administration of the candidate drug or the placebo; and (h) determining if the candidate drug modifies the metabolism profile over the course of the trial.

In another embodiment, the present invention includes a method for selecting a therapy for improved cognition or prevention of cognitive loss using one or more neurotrophic factor therapies (agonists) comprising: obtaining a sample from a subject; measuring one or more biomarkers in the sample selected from BDNF, NGF, TN-3, CNTF, GDNF, LIF, and GGF; comparing the level of the one or more biomarkers within a sample of patients suffering from cognitive loss; dividing the level of expression of the one or more biomarkers as being either high neurotrophic or low neurotrophic; and selecting a course of treatment for the subject based on whether the subject is selected as being high neurotrophic endophenotype or low neurotrophic endophenotype. In one aspect, the method further comprises the steps of: generating a high and a low neurotrophic endophenotype by determining the level of expression of 2, 3, 4, 5, 6, or 7 biomarkers selected from brain derived neurotrophic factor (BDNF), nerve growth factor (NGF), tenascin 3 (TN-3), ciliary neurotrophic factor (CNTF), glial cell derived neurotrophic factor (GDNF), leukemia inhibitory factor (LIF), and neuregulin-1 (GGF); and determining the high and low neurotrophic endophenotypes by determining the level of expression of 2, 3, 4, 5, 6, or 7 more biomarkers. In one aspect, the neurotrophic profile is generated using learning machines (random forest, support vector machines), clustering algorithms (factor analysis, principal component analysis), summation of values, or other methods to generate a neurotrophic score across multiple measures. In another aspect, the high end of the score across multiple markers is reflective of the high neurotrophic endophenotype and the low end as the low neurotrophic endophenotype with all others falling in a middle endophenotype. In another aspect, if the subject is scored in the low neurotrophic group a neurotrophic-factor treatment is indicated to maintain cognitive ability, and if the subject is scored in a high neurotrophic group then a neurotrophic-factor treatment may be indicated to boost cognitive ability, but may be contraindicated in some patients. In another aspect, at least one of the biomarker measurements is obtained by a method selected from the group consisting of immunoassay and enzymatic activity assay. In another aspect, the sample is serum or plasma. In another aspect, the cognitive dysfunction is a disease or condition selected from Alzheimer's Disease, Parkinson's Disease, Down's syndrome, Frontotemporal dementia, Dementia with Lewy Bodies, Multiple sclerosis, traumatic brain injury, depression, schizophrenia, bipolar disease (and other mental illness), diabetes, hypertension, stroke, heart attack, dyslipidemia, other conditions/diseases or aging. In another aspect, cognition is "normal" but patients are deemed "at risk" based on their proinflammatory endophenotype. In another aspect, the level of expression of the various proteins is measured by at least one of fluorescence detection, chemiluminescence detection, electrochemiluminescence detection and patterned arrays, reverse transcriptase-polymerase chain reaction, antibody binding, fluorescence activated sorting, detectable bead sorting, antibody arrays, microarrays, enzymatic arrays, receptor binding arrays, allele specific primer extension, target specific primer extension, solid-phase binding arrays, liquid phase binding arrays, fluorescent resonance transfer, or radioactive labeling. In another aspect, the high and low end of the neurotrophic group is determined by specifically determining the level of expression of BDNF, NGF, and TN-3. In another aspect, the neurotrophic endophenotype may be treated with one of more of the following non-limiting examples of therapeutic agents: Neurotrophic factor agonist, exercise therapy, brain derived neurotrophic factor (BDNF) and BDNF agonists, selective serotonin reuptake inhibitors, selective serotonin 2C (5-HT2C) antagonists, serotonin-norepinephrine reuptake inhibitors, tricyclic, combined exercise and medications, glial-cell derived neurotrophic factor (GDNF) and GDNF agonists.

In another embodiment, the present invention includes a method for selecting patient therapy for improved cognition or prevention of cognitive loss comprising: obtaining a sample from a subject; measuring the level of expression of brain derived neurotrophic factor (BDNF), nerve growth factor (NGF), and tenascin 3 (TN-3); determining the tertile of the level of expression of the these three biomarkers; and depending on the level of expression dividing the level of expression of the two or more markers as being either high neurotrophic endophenotype or low neurotrophic endophenotype; and selecting a course of treatment for the subject based on whether the subject is selected as being high neurotrophic endophenotype or low neurotrophic endophenotype, wherein the tertile is determined by: scoring the tertile scores for both markers to generate a score with a range from two to six, assigning a lower score (i.e., 3) to the low end of a neurotrophic, assigning a highest score (i.e., 9) score was assigned to a high end of the neurotrophic, with all other scores falling in a middle score. In one aspect, if the subject is scored in the tertile that is scored as a high neurotrophic a neurotrophic-factor treatment may be indicated to preserve remaining cognitive ability, and if the subject is scored in a low neurotrophic endophenotype then a neurotrophic-factor treatment (agonist) is indicated to improve and maintain cognition. In another aspect, the sample is serum or plasma. In another aspect, the cognitive dysfunction is a disease or condition selected from Alzheimer's Disease, Parkinson's Disease, Down's syndrome, Frontotemporal dementia, Dementia with Lewy Bodies, Multiple sclerosis, traumatic brain injury, depression, schizophrenia, bipolar disease (and other mental illness), diabetes, hypertension, stroke, heart attack, dyslipidemia, other conditions/diseases or aging. In another aspect, cognition is "normal" but patients are deemed "at risk" based on their pro-inflammatory endophenotype. In another aspect, the level of expression of the various proteins is measured by at least one of fluorescence detection, chemiluminescence detection, electrochemiluminescence detection and patterned arrays, reverse transcriptase-polymerase chain reaction, antibody binding, fluorescence activated sorting, detectable bead sorting, antibody arrays, microarrays, enzymatic arrays, receptor binding arrays, allele specific primer extension, target specific primer extension, solid-phase binding arrays, liquid phase binding arrays, fluorescent resonance transfer, or radioactive labeling.

In another embodiment, the present invention includes a method of determining the effectiveness of a candidate drug that impacts the neurotrophic system to evaluate the candidate drug believed to be useful in treating and/or preventing cognitive loss, the method comprising: (a) measuring one or more biomarkers in a sample of serum or plasma obtained from a subject suspected of having cognitive loss selected from BDNF, NGF, TN-3, CNTF, GDNF, LIF, and GGF; (b) administering the candidate drug to a first subset of the patients, and a placebo to a second subset of the patients; (c) generating the neurotrophic endophenotype groups using one or a combination of the one or more biomarkers; (d) determining the tertile of the level of expression of the one or more biomarkers; and depending on the level of expression dividing the level of expression of the one or more markers as being either high neurotrophic or low neurotrophic; (e) determining if baseline neurotrophic endophenotype group predicted treatment response such that the high and low neurotrophic endophenotype groups responded differentially than the middle neurotrophic endophenotype group; (f) repeating step (a) after the administration of the candidate drug or the placebo; (g) determining if the candidate drug modifies the neurotrophic profile over the course of the trial; and (h) determining if change in the pro neurotrophic profile over the course of the trial predicted a positive response, a negative response, or a no treatment response, and if a statistically significant treatment response for cognitive loss with the candidate drug is obtained. In one aspect, the method further comprises the steps of obtaining one or more additional blood samples from the patient after a pre-determined amount of time and comparing the levels of the biomarkers from the one or more additional samples to determine progression of cognitive loss. In one aspect, the method further comprises the steps of treating the patient for a pre-determined period of time, obtaining one or more additional blood samples from the patient after the pre-determined amount of time and comparing the levels of the biomarkers from the one or more additional samples to determine progression of cognitive loss.

In another embodiment, the present invention includes a method of determining the effectiveness of a candidate drug that impacts the neurotrophic system to evaluate the candidate drug believed to be useful in treating and/or preventing cognitive loss, the method comprising: (a) measuring the serum or plasma based levels of BDNF, NGF, and TN-3; (b) administering the candidate drug to a first subset of the patients, and a placebo to a second subset of the patients; (c) generating the neurotrophic groups using a combination of BDNF, NGF, and TN-3 for the first and second subset of patients; (d) determining the tertile of the level of expression of BDNF, NGF, and TN-3 in the first and second subset of patients; (e) dividing the level of expression of BDNF, NGF, and TN-3 as being either high neurotrophic or low neurotrophic depending on the level of expression of BDNF, NGF, and TN-3; (f) determining if baseline neurotrophic group predicted treatment response such that the high neurotrophic group responded differentially than the low neurotrophic group, (g) repeating step (a) after the administration of the candidate drug or the placebo; and (h) determining if the candidate drug modifies the neurotrophic profile over the course of the trial. In one aspect, the method further comprises the step of determining if change in the pro neurotrophic profile based on the one or more neurotrophic biomarkers over the course of the trial predicted both positive and negative treatment response as well as no treatment response and if a statistically significant treatment response for the candidate drug was achieved as a primary or secondary outcome of the clinical trial. In another aspect, the method further comprises the steps of obtaining one or more additional blood samples from the patient after a pre-determined amount of time and comparing the levels of the one or more neurotrophic biomarkers from the one or more additional samples to determine progression of cognitive loss. In one aspect, the method further comprises the steps of: treating the patient for a pre-determined period of time, obtaining one or more additional blood samples from the patient after the pre-determined amount of time and comparing the levels of the biomarkers from the one or more additional samples to determine progression of cognitive loss.

In another embodiment, the present invention includes a method for selecting a therapy for improved cognition or prevention of cognitive loss using one or more antidepressant therapies comprising: obtaining a sample from a subject; measuring the depressive endophenotype of cognitive dysfunction (DepE) scores; and selecting a course of treatment for the subject based on whether the subject is elevated on DepE score. In one aspect, the method further comprises the steps of: generating a DepE score via administration of the select depressive items; and determining elevation on DepE. In one aspect, the DepE profile is generated using learning machines (random forest, support vector machines), clustering algorithms (factor analysis, principal component analysis), summation of values, or other methods to generate a depressive endophenotype across multiple measures. In another aspect, the elevation of DepE identifies those eligible for antidepressant therapy for improved cognition. In another aspect, if the subject is scored elevated on DepE an antidepressant treatment is indicated. In another aspect, the cognitive dysfunction is a disease or condition selected from Alzheimer's Disease, Parkinson's Disease, Down's syndrome, Frontotemporal dementia, Dementia with Lewy Bodies, Multiple sclerosis, traumatic brain injury, depression, schizophrenia, bipolar disease (and other mental illness), diabetes, hypertension, stroke, heart attack, dyslipidemia, other conditions/diseases or the aging process itself. In another aspect, cognition is "normal" but patients are deemed "at risk" based on their pro-inflammatory endophenotype. In another aspect, the depressive endophenotype may be treated with one of more of the following non-limiting examples of therapeutic agents: Antidepressant medications, selective serotonin reuptake inhibitors, selective serotonin 2C (5-HT2C) antagonists, serotonin-norepinephrine reuptake inhibitors, and tricyclic antidepressants combined exercise and medications.

In one embodiment, the present invention also includes a method of determining the effectiveness of a candidate a drug that impacts depression to evaluate the candidate drug believed to be useful in treating and/or preventing cognitive loss, the method comprising: (a) screening patients into a clinical trial based on elevated DepE scores; (b) administering the candidate drug to a first subset of the patients, and a placebo to a second subset of the patients; (c) determining if baseline DepE scores predicted treatment response such that the high DepE group responded differentially than the low DepE group; (d) repeating step (a) after the administration of the candidate drug or the placebo; (e) determining if the candidate drug modifies the DepE scores over the course of the trial; and (f) determining if change in the DepE scores over the course of the trial predicted a positive response, a negative response, or a no treatment response, and if a statistically significant treatment response with the candidate drug is obtained.

In another embodiment, the present invention includes a method for selecting a therapy for improved cognition or prevention of cognitive loss using one or more endophenotypes comprising: obtaining a sample from a subject; measuring biomarkers that differentiate between an inflammatory, a metabolic, a neurotrophic, and a depressive endophenotype; and selecting a course of treatment for the subject based on whether the subject is scored as having a high or a low endophenotype for one or more of the inflammatory, a metabolic, a neurotrophic, and a depressive endophenotypes. In another aspect, the endophenotype profile is generated using learning machines (random forest, support vector machines), clustering algorithms (factor analysis, principal component analysis), summation of values, or other methods to generate an endophenotypescore across multiple measures. In another aspect, if the subject is scored elevated for inflammatory endophenotype an anti-inflammatory treatment is indicated. In another aspect, if the subject is scored elevated for metabolic endophenotype and anti-metabolic treatment is indicated. In another aspect, if the subject is scored elevated for neurotrophic endophenotype a neurotrophic treatment is indicated. In another aspect, if the subject is scored elevated for depression emdophenotype an anti-depressant treatment is indicated. In another aspect, the cognitive dysfunction is a disease or condition selected from Alzheimer's Disease, Parkinson's Disease, Down's syndrome, Frontotemporal dementia, Dementia with Lewy Bodies, Multiple sclerosis, traumatic brain injury, depression, schizophrenia, bipolar disease (and other mental illness), diabetes, hypertension, stroke, heart attack, dyslipidemia, other conditions/diseases or the aging process itself. In another aspect, cognition is "normal" but patients are deemed "at risk" based on their pro-inflammatory endophenotype.

In another embodiment, the present invention includes a method of performing a clinical trial for a drug that impacts depression is useful in treating and/or preventing cognitive loss, the method comprising: (a) screening patients into a clinical trial based on elevated biomarkers for an inflammatory, a metabolic, a neurotrophic, and a depressive endophenotype; (b) administering a candidate drug to a first subset of the patients, and a placebo to a second subset of the patients; (c) determining if baseline endophenotype scores predicted treatment response such that the high endophenotype group responded differentially than the low endophenotype group; (d) repeating step (a) after the administration of the candidate drug or the placebo; (e) determining if the candidate drug modifies the endophenotype scores over the course of the trial; and (f) determining if change in the endophenotype scores over the course of the trial predicted a positive response, a negative response, or a no treatment response, and if a statistically significant treatment response with the candidate drug is obtained.

In another embodiment, the present invention includes an apparatus for selecting a therapy for improved cognition or preventing cognitive loss using one or more endophenotypes comprising: a biomarker array that detects biomarkers and computerized questions/cognitive assessments from a sample for two or more endophenotypes selected from an inflammatory, a metabolic, a neurotrophic, and a depressive endophenotype; a processor/algorithm that obtains a biomarker and questionnaire/cognitive test results expression output from the biomarker array, wherein an endophenotype profile is generated using learning machines (random forest, support vector machines), clustering algorithms (factor analysis, principal component analysis), summation of values, or other methods to generate an endophenotypescore across multiple measures; and an output that indicates a course of treatment for the subject based on whether the subject is scored as having a high or a low endophenotype for two or more of the inflammatory, metabolic, neurotrophic, or depressive endophenotypes. In another aspect, if the subject is scored elevated for inflammatory endophenotype an anti-inflammatory treatment is indicated. In another aspect, if the subject is scored elevated for metabolic endophenotype and anti-metabolic treatment is indicated. In another aspect, if the subject is scored altered (elevated and/or suppressed) for neurotrophic endophenotype a neurotrophic treatment is indicated. In another aspect, if the subject is scored elevated for depression endophenotype an anti-depressant treatment is indicated. In another aspect, the cognitive dysfunction is a disease or condition selected from Alzheimer's Disease, Parkinson's Disease, Down's syndrome, Frontotemporal dementia, Dementia with Lewy Bodies, Multiple sclerosis, traumatic brain injury, depression, schizophrenia, bipolar disease (and other mental illness), diabetes, hypertension, stroke, heart attack, dyslipidemia, other conditions/diseases or the aging process itself. In another aspect, cognition is "normal" but patients are deemed "at risk" based on their pro-inflammatory endophenotype.

In another embodiment, the present invention includes a method for selecting patients to determine the effectiveness of a candidate drug comprising: generating a prediction model dataset by: pre-selecting a level of treatment response selected from positive, negative and no response for a patient dataset within an endophenotype; obtaining the patient dataset based on the endophenotype selected; and separating the patient dataset into a responder patient dataset, non-responder patient dataset and adverse responder patient dataset; applying the prediction model blindly to a second clinical trial dataset to predict outcomes; and determining the efficacy of the prediction model in predicting treatment responders, non-responders and adverse responders in a third trial, wherein the efficacy for the third trial is increased by only evaluating a patient outcome from the responder patient dataset. In one aspect, the one or more outcome variable datasets are preselected based on the endophenotypes. In another aspect, the method further comprises the step of determining a depressive endophenotype and then evaluating: quality of life, daily living ability, or depression rates. In another aspect, the method further comprises selecting one or more additional endophenotypes for evaluation. In another aspect, the method further comprises the step of selecting one or more patients for targeted therapy, designing a new clinical trial that specifically targets only those patients most likely to respond, or both.

In another embodiment, the present invention includes a method for selecting a treatment or prevention of cognitive loss comprising: obtaining a patient endophenotype dataset; selecting the patient for further evaluation if the patient endophenotype dataset comprises a proinflammatory endophenotype; and obtaining cognitive impairment dataset, wherein positivity for both a proinflammatory endophenotypes and the cognitive impairment dataset is indicative of beta amyloid (Aβ) positivity. In one aspect, the method further comprises the step of obtaining an APOE4 genotype. In another aspect, the method further comprises the step of identifying cognitive loss among those without frank impairment.

In another embodiment, the present invention includes a method for selecting a treatment or prevention of cognitive loss from chronic kidney disease comprising: obtaining a sample from a patient suspected of having a chronic kidney disease; determining the level of expression of fatty acid binding protein (FABP3), beta 2 microglobulin, pancreatic polypeptide (PPY), sTNFR1, CRP, VCAM1, thrombopoeitin (THPO), α2 macroglobulin (A2M), exotaxin 3, tumor necrosis factor α, tenascin C, IL5, IL6, IL7, IL10, IL18, I309, Factor VII, TARC, SAA, and ICAM1; calculating a patient cognitive impairment endophenotype dataset using the level of expression; and selecting the patient for further evaluation if the patient endophenotype dataset comprises a proinflammatory endophenotype. In one aspect, the method further comprises the step of obtaining an APOE4 genotype. In another aspect, the method further comprises step of identifying cognitive loss among those without frank impairment. In another aspect, the patients are of Hispanic descent. In another aspect, the method further comprises the step of selecting a course of treatment for the chronic kidney disease, the cognitive loss or both based on the patient endophenotype dataset.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1:
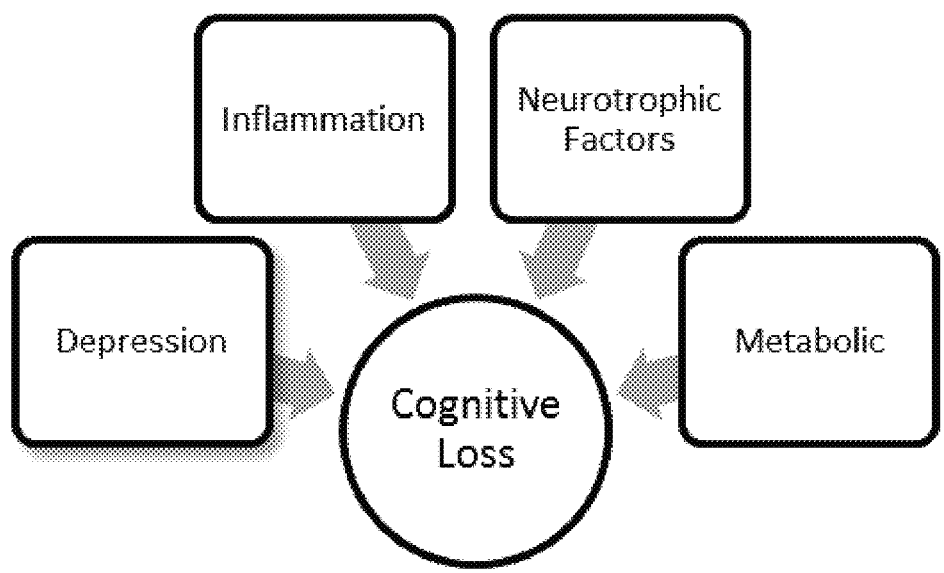
FIG. 1 shows four endophenotypes for cognitive loss.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the phrase "neurological disease" refers to a disease or disorder of the central nervous system and many include, e.g., neurodegenerative disorders such as AD, Parkinson's disease, mild cognitive impairment (MCI) and dementia and neurological diseases include multiple sclerosis, neuropathies. The present invention will find particular use in treating cognitive dysfunction associated with AD and other neurodegenerative disorders such as Parkinson's Disease, Frontotemporal dementia, Dementia with Lewy Bodies, and Down's syndrome.

As used herein, the terms "Alzheimer's patient", "AD patient", and "individual diagnosed with AD" all refer to an individual who has been diagnosed with AD or has been given a probable diagnosis of Alzheimer's Disease (AD).

As used herein, the terms "Parkinson's disease patient", and "individual diagnosed with Parkinson's disease" all refer to an individual who has been diagnosed with PD or has been given a diagnosis of Parkinson's disease.

As used herein, the terms "Frontotemporal dementia", and "individual diagnosed with frontotemporal dementia" all refer to an individual who has been diagnosed with FTD or has been given a diagnosis of FTD.

As used herein, the term "Dementia with Lewy bodies" (DLB), and "individual diagnosed with DLB" all refer to an individual who has been diagnosed with DLB or has been given a diagnosis of DLB.

As used herein, the term "Down's syndrome" (DS), and "individual diagnosed with Down's syndrome" all refer to an individual who has been diagnosed with DS or has been given a diagnosis of DS.

As used herein, the phrase "neurological disease biomarker" refers to a biomarker that is a neurological disease diagnosis biomarker.

As used herein, the term "neurological disease biomarker protein", refers to any of: a protein biomarkers or substances that are functionally at the level of a protein biomarker.

As used herein, the terms "cognition", "cognitive ability", "memory", "language" and the like are used interchangeably to refer to an individual's ability to perform cognitive abilities and the dysfunction of those abilities that may be as a result of a diagnosis of MCI, AD, DLB, FTD, DLB, Multiple Sclerosis (MS), PD, or other neurological disease as well as other medical and psychiatric conditions including, but not limited to, diabetes, hypertension, dyslipidemia, metabolic syndrome, depression, traumatic brain injury, schizophrenia, bipolar disease, as well as the cognitive slowing/decline associated with the aging process itself.

As used herein, methods for "aiding treatment" refer to methods that assist in making a clinical determination regarding the course of treatment of cognitive dysfunction associated with the neurological disease (e.g., AD, PD, DLB, FTD, DS or MCI), and may or may not be conclusive with respect to the definitive diagnosis.

As used herein, the term "stratifying" refers to sorting individuals into different classes or strata based on the features of a neurological disease. For example, stratifying a population of individuals with Alzheimer's disease involves assigning the individuals on the basis of the severity of the disease (e.g., mild, moderate, advanced, etc.).

As used herein, the term "predicting" refers to making a finding that an individual has a significantly enhanced probability of developing a certain neurological disease.

As used herein, "biological fluid sample" refers to a wide variety of fluid sample types obtained from an individual and can be used in a diagnostic or monitoring assay. Biological fluid sample include, e.g., blood, cerebral spinal fluid (CSF), urine and other liquid samples of biological origin. Commonly, the samples are treatment with stabilizing reagents, solubilization, or enrichment for certain components, such as proteins or polynucleotides, so long as they do not interfere with the analysis of the markers in the sample.

As used herein, a "blood sample" refers to a biological sample derived from blood, preferably peripheral (or circulating) blood. A blood sample may be, e.g., whole blood, serum or plasma. In certain embodiments, serum is preferred as the source for the biomarkers as the samples are readily available and often obtained for other sampling, is stable, and requires less processing, thus making it ideal for locations with little to refrigeration or electricity, is easily transportable, and is commonly handled by medical support staff.

As used herein, a "normal" individual or a sample from a "normal" individual refers to quantitative data, qualitative data, or both from an individual who has or would be assessed by a physician as not having a disease, e.g., a neurological disease. Often, a "normal" individual is also age-matched within a range of 1, 2, 3, 4, 5, 6, 7, 8, 9 or 10 years with the sample of the individual to be assessed.

As used herein, the term "treatment" refers to the alleviation, amelioration, and/or stabilization of symptoms, as well as delay in progression of symptoms of a particular disorder. For example, "treatment" of AD includes any one or more of: (1) elimination of one or more symptoms of AD, (2) reduction of one or more symptoms of AD, (4) stabilization of the symptoms of AD (e.g., failure to progress to more advanced stages of AD), and (5) delay in onset of one or more symptoms of AD delay in progression (i.e., worsening) of one or more symptoms of AD; and (6) delay in progression (i.e., worsening) of one or more symptoms of AD.

As used herein, the term "endophenotype" refers to a subgroup of patients within a broader category, which can be defined by biological, cognitive, or psychological/questionnaire data. FIG. 1 shows four endophenotypes for cognitive loss. For example, within patients diagnosed with traumatic brain injury (TBI) who are suffering from cognitive loss, those TBI patients may be subdivided into groups based on a pro-inflammatory endophenotype, neurotrophic factor endophenotype, metabolic endophenotype and even a depressive endophenotype.

As used herein, the term "fold difference" refers to a numerical representation of the magnitude difference between a measured value and a reference value, e.g., an AD biomarker, a Parkinson's biomarker, a dementia biomarker, or values that allow for the differentiation of one or more of the neurological diseases. Typically, fold difference is calculated mathematically by division of the numeric measured value with the numeric reference value. For example, if a measured value for an AD biomarker is 20 nanograms/milliliter (ng/ml), and the reference value is 10 ng/ml, the fold difference is 2 (20/10=2). Alternatively, if a measured value for an AD biomarker is 10 nanograms/milliliter (ng/ml), and the reference value is 20 ng/ml, the fold difference is 10/20 or −0.50 or −50%).

As used herein, a "reference value" can be an absolute value, a relative value, a value that has an upper and/or lower limit, a range of values; an average value, a median value, a mean value, or a value as compared to a particular control or baseline value. Generally, a reference value is based on an individual sample value, such as for example, a value obtained from a sample from the individual with e.g., a neurological disease such as AD, Parkinson's Disease, or dementia, preferably at an earlier point in time, or a value obtained from a sample from an neurological disease patient other than the individual being tested, or a "normal" individual, that is an individual not diagnosed with AD, Parkinson's Disease, or dementia. The reference value can be based on a large number of samples, such as from AD patients, Parkinson's Disease patients, dementia patients, or normal individuals or based on a pool of samples including or excluding the sample to be tested.

As used herein, the phrase "a pre-determined amount of time" is used to describe the length of time between measurements that would yield a statistically significant result, which in the case of disease progression for cognitive loss can be 7 days, 2 weeks, one month, 3 months, 6 months, 9 months, 1 year, 1 year 3 months, 1 year 6 months, 1 year 9 months, 2 years, 2 years 3 months, 2 years 6 months, 2 years 9 months, 3, 4, 5, 6, 7, 8, 9 or even 10 years and combinations thereof.

As used herein, the phrases "neurocognitive screening tests", or "cognitive test" are used to describe one or more tests known to the skilled artisan for measuring cognitive status or impairment and can include but is not limited to: a 4-point clock drawing test, an verbal fluency test, trail making test, list learning test, and the like. The skilled artisan will recognize and know how these tests can be modified, how new tests that measure similar cognitive function can be developed and implemented for use with the present invention.

Cognitive loss is common among the aging/elderly population. Approximately 10-12% of all individuals age 65 and above suffer from Alzheimer's disease with another approximately 20% suffering from mild cognitive impairment (MCI), which is a prodromal phase to Alzheimer's disease. Additionally, cognitive loss is commonly associated with other neurodegenerative (e.g. Parkinson's disease, frontotemporal dementia), neurological (e.g. traumatic brain injury, multiple sclerosis), psychiatric (e.g. depression, bipolar, schizophrenia) and other medical conditions (e.g. diabetes, hypertension, dyslipidemia). On the other hand, the "one-size-fits-all" approach to treating cognitive loss among adults and elders has largely been a failure. For example, all clinical trials focusing on beta amyloid protein within Alzheimer's disease have failed in Phase III testing with no new medications approved for this disease in decades. Additionally, while there are well-established depression—cognition and diabetes—cognition links, trials focusing on disease specific interventions have been of limited benefit. These failures led to the present discovery, namely, that there are many underlying biological reasons for cognitive loss and that these systems may be largely "disease" irrelevant. For example, inflammation is related to many diseases (e.g. Alzheimer's disease, Parkinson's disease, cancer, multiple sclerosis, diabetes, TBI), which the present inventors have recognized are linked to poorer cognition across diseases. Therefore, the present inventors have subgrouped patients who are at increased risk for cognitive loss related to underlying dysfunction of the inflammatory, and other systems, and to treatment regimens that improve or prevent such cognitive loss across disease conditions. To date, there have been no strategies for prevention of cognitive loss that have been proven effective.

The present inventors have developed an endophenotype approach to treating and preventing cognitive loss among aging population. The term endophenotype[1] has been discussed frequently in psychiatry and they provide a way for identifying subgroups of clinical phenotypes[2]. The present invention demonstrates four distinct endophenotypes that can be used to guide cognitive impairment therapy: inflammatory[3,4], neurotrophic factor[5], depressive[6] and metabolic[7] endophenotypes of cognitive loss. Endophenotypes of cognitive loss have also been identified based on neuropathology[8], neuroimaging[9,10], genetics[11], and cerebrospinal fluid markers[12]. The inventors provide herein four endophenotypes specifically designed to guide therapy and exemplary therapies for use with the invention.

Pro-inflammatory endophenotype. When providing treatment for those subjects identified with the pro-inflammatory endophenotypes, the treatment can include the following. Nonsteroidal anti-inflammatory drugs (NSAIDs): Non-selective NSAIDs—non-selective NSAIDs would be selected for those patients falling into the high end of the proinflammatory endophenotype. As shown herein, non-selective NSAIDs (naproxen) were the superior treatment to selective NSAIDs (celecoxib). Non-selective NSAIDs can be tested with anyone falling within the high end of the proinflammatory endophenotype.

Selective NSAIDs: selective NSAIDs (e.g. celecoxib) can be tested with those falling within the high end of the proinflammatory endophenotype.

Steroids: Many steroids, glucocorticoids, have anti-inflammatory properties and can be considered for those patients falling within the high end of the pro-inflammatory endophenotype.

Immune Selective Anti-Inflammatory Derivatives (ImSAIDs): ImSAIDs can be considered for patients falling within the high end of the proinflammatory endophenotype.

Anti-TNF medications can be specifically utilized for those within the high end of the proinflammatory endophenotype where TNFα weighs most heavily.

Anti-IL5 drugs can be utilized for those within the high end of the proinflammatory endophenotype where IL-5 weighs most heavily.

CRP-lowering agents can be selectively utilized for those in the high end of the proinflammatory endophenotype where CRP weighs most heavily.

Metabolic Endophenotype.

When providing treatment for those subjects identified with the metabolic endophenotypes anti-diabetic medications can be utilized for those falling within the low or high end of the metabolic endophenotype, depending on the mechanism of action of the drug.

Insulin would be utilized for those whose metabolic endophenotype weighs insulin heavily. Insulin may be utilized also for those whose metabolic endophenotype weighs glucose levels most heavily.

GLP-1 medications would be utilized for those whose metabolic endophenotype weighs GLP-1 most heavily. In the inventors' prior work, GLP-1 was higher among those with cognitive dysfunction; however, higher levels of GLP-1 was associated with better memory and therefore would be administered for treatment of cognitive problems among those with cognitive loss and prevention of cognitive loss among cognitively normal elders.

Amylin-related medications can be utilized for those whose metabolic endophenotype weighs amylin most heavily.

Oral hypoglycemics can be tested among any patients who are in the high end of the metabolic endophenotype.

Neurotrophic Endophenotype.

When providing treatment for those subjects identified with the neurotrophic endophenotypes neurotrophic factor agonists can be examined for improved cognitive function and prevention of cognitive loss among those in the low end of the neurotrophic endophenotype. Neurotrophic factor agonists can be examined for cognitive improvement among those in the high end of the neurotrophic endophenotype. It is unlikely that those in the middle group of the neurotrophic endophenotype will experience cognitive benefit or decline from such treatments.

Exercise therapy can be prescribed to any patients who fall into the low end of the neurotrophic endophenotype for prevention or treatment of cognitive loss as well as for improvement of cognitive loss among those in the high end of the neurotrophic endophenotype.

BDNF and BDNF agonists would be utilized for those patients in the low end of the neurotrophic endophenotype for improved cognition as well as prevention of cognitive loss. Such medications would be utilized for treating cognitive loss among the high end of the endophenotype. Selective serotonin reuptake inhibitors, selective serotonin 2C (5-HT2C) antagonists, serotonin-norepinephrine reuptake inhibitors, and tricyclic antidepressants have been found to increase BDNF levels and may be particularly useful in treating and/or preventing cognitive loss for those whose neurotrophic endophenotype weighs BDNF most heavily.

Combined exercise and medications such as selective serotonin reuptake inhibitors, selective serotonin 2C (5-HT2C) antagonists, serotonin-norepinephrine reuptake inhibitors, and tricyclic antidepressants have been found to increase BDNF levels and may be particularly useful in treating and/or preventing cognitive loss for those whose neurotrophic endophenotype weighs BDNF most heavily.

GDNF and GDNF agonists would be utilized for those patients in the low end of the neurotrophic endophenotype for improved cognition as well as prevention of cognitive loss. Such medications would be utilized for treating cognitive loss among the high end of the endophenotype.

Depressive Endophenotype.

When providing treatment for those subjects identified with the depressive endophenotypes antidepressant medications and/or therapy can be utilized for those who score elevated on the depressive endophenotype of cognitive loss (DepE) for treatment and/or prevention of cognitive dysfunction.

Selective serotonin reuptake inhibitors, selective serotonin 2C (5-HT2C) antagonists, serotonin-norepinephrine reuptake inhibitors, and tricyclic antidepressants have been found related to cognitive functioning may be useful in treating and/or preventing cognitive loss for those whose score elevated on DepE scores.

Combined exercise and medications such as selective serotonin reuptake inhibitors, selective serotonin 2C (5-HT2C) antagonists, serotonin-norepinephrine reuptake inhibitors, and tricyclic antidepressants may be particularly useful in treating and/or preventing cognitive loss for those who score elevated on the DepE.

For those subjects with a proinflammatory endophenotype that weighs IL-6 most heavily, selective serotonin reuptake inhibitors, selective serotonin 2C (5-HT2C) antagonists, serotonin-norepinephrine reuptake inhibitors, and tricyclic antidepressants may be particularly useful in treating and/or preventing cognitive loss for those who score elevated on the DepE.

For those subjects with an proinflammatory endophenotype that weights IL-6 and/or TNFα most heavily, combined exercise and antidepressant therapy (selective serotonin reuptake inhibitors, selective serotonin 2C (5-HT2C) antagonists, serotonin-norepinephrine reuptake inhibitors, and tricyclic antidepressants) may be particularly useful in treating and/or preventing cognitive loss for those who score elevated on the DepE.

Proinflammatory Endophenotype.

Cognitive dysfunction and decline is a major source of morbidity and mortality in the U.S. and is associated with greater health care cost, decreased treatment compliance, lost wages (patient and family), decreased productivity, poorer quality of life and gradual loss of independence. The most prominent form of cognitive loss is dementia of the Alzheimer's type; however, cognitive loss is also associated with traumatic brain injury (TBI), multiple sclerosis (MS), Parkinson's disease (PD), depression, schizophrenia, as well as many other disorders/diseases. Interestingly, inflammation is a common biological pathway that has been linked with each of these conditions as well as cognitive loss. Additionally, epidemiological studies suggest that use of anti-inflammatory medications is associated with decreased risk for cognitive loss/dementia as well as increased cognitive functioning among various disease states (e.g. TBI) though these results have been inconsistent and with many clinical trials ending in failure. To date, no prior work has been undertaken to develop a personalized medicine approach to identification of which specific patients should or should not be placed on anti-inflammatory medications in order to improve cognition. The novel method of the present invention was explicitly developed as a personalized medicine approach that identifies not only the sub-population of individuals who should be placed on anti-inflammatory medications for cognitive enhancing benefits, but equally important, which sub-population should not be placed on these medications as it is associated with greater cognitive loss. This new method can be implemented in clinical trials and practice to improve/stabilize cognition among a select sub-population of patients as well as screen out patients that should not be placed on anti-inflammatory medications due to risk of increased cognitive decline. The present inventors, have discussed the existence of a proinflammatory endophenotypes, however, this work for the first time provides a distinct endophenotypes, a combination of endophenotypes, and/or a critical therapeutic regimen as a result of the endophenotype[3,4,15,16]

In order to determine if the proinflammatory endophenotype predicted treatment response, baseline plasma samples were analyses from a previously conducted trial of the Alzheimer's Disease Cooperative Study (ADCS, Aisen et al 2003, JAMA).

Baseline plasma samples were assayed using enhanced chemiluminescence (ECL) for a range of inflammatory markers. The pro-inflammatory profile was generated using CRP and TNFα. Additional markers can be used to improve the already robust results shown herein. The frequency of the low, middle (referent group) and high ends of the pro-inflammatory profile are presented below.

TABLE 1

|   | Arm2 |   | Frequency | Percent | Valid Percent | Cumulative Percent |
|---|---|---|---|---|---|---|
| placebo | Valid | Low | 6 | 8.3 | 11.1 | 11.1 |
|   |   | Middle | 43 | 59.7 | 79.6 | 90.7 |
|   |   | High | 5 | 6.9 | 9.3 | 100.0 |
|   |   | Total | 54 | 75.0 | 100.0 |   |
|   | Missing | System | 18 | 25.0 |   |   |
|   | Total |   | 72 | 100.0 |   |   |
| treatment | Valid | Low | 7 | 9.1 | 11.1 | 11.1 |
|   |   | Middle | 46 | 59.7 | 73.0 | 84.1 |
|   |   | High | 10 | 13.0 | 15.9 | 100.0 |
|   |   | Total | 63 | 81.8 | 100.0 |   |
|   | Missing | System | 14 | 18.2 |   |   |
|   | Total |   | 77 | 100.0 |   |   |

Figure 2:
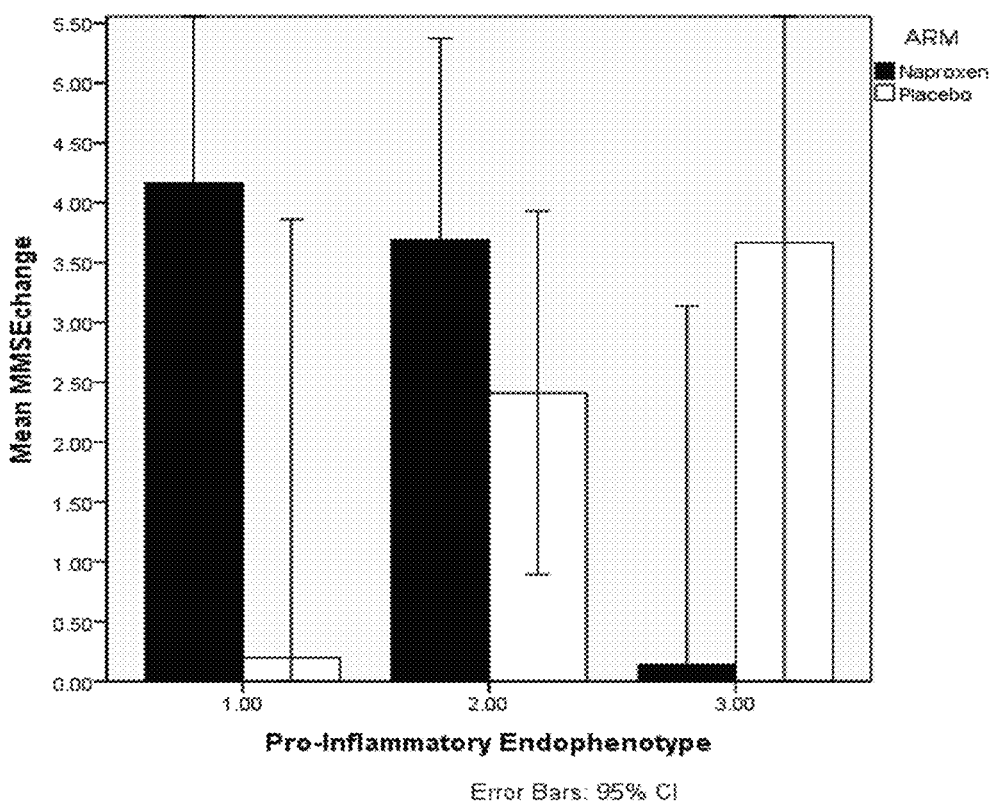
FIG. 2 is a graph that shows the effect of treating subjects with naproxen and a placebo with three different pro-inflammatory endophenotypes.

When looking at change in MMSE scores over the 12 month period of the trial, the findings were as follows: Placebo group—(a) those in the low end of the pro-inflammatory profile were stable over 12 months (stable in disease severity and cognitive functioning) when compared to the high end and the referent group (i.e. middle group), (b) those in the high end declined significantly over 12 months when compared to the referent group and the low end of the pro-inflammatory profile. Treatment group—(a) those in the low end of the pro-inflammatory profile (group 1 in FIG. 2) who were treated with an anti-inflammatory drug declined significantly faster (i.e. disease severity and cognition) when compared to the referent group (i.e. middle group; group 2 in FIG. 2)), (b) those in the high end (group 3 in FIG. 2) were stable over 12 months when treated with an anti-inflammatory drug when compared to the low end of the pro-inflammatory profile and the referent group. Therefore, treatment is indicated among those in the high end of the proinflammatory endophenotypes, but contraindicated among those in the low end of the proinflammatory endophenotype.

Figure 3:
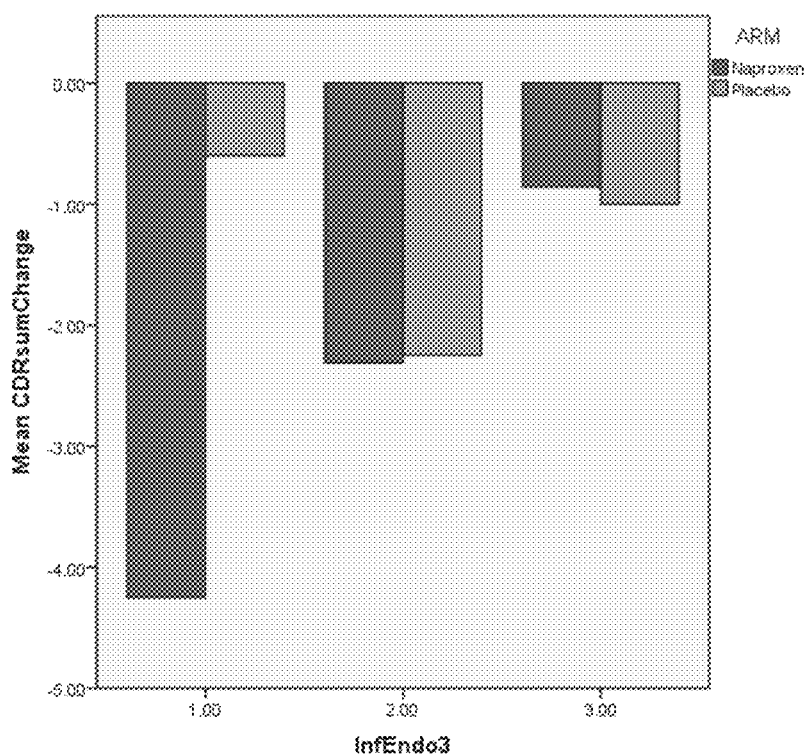
FIG. 3 is a graph that shows the progression of disease when treating subjects with naproxen and a placebo with three different pro-inflammatory endophenotypes.

When considering disease severity (i.e., clinical dementia rating (CDR) Sum of Boxes [CDRSum]), the same was found. See FIG. 3. Specifically, those in the low end of the pro-inflammatory profile who were treated with an anti-inflammatory drug progressed in disease severity more rapidly over 12 months than any other group whereas those who were in that same biomarker-defined group declined minimally over 12 months if left untreated. On the other hand, those in the high end who were treated declined less than those who were untreated though the magnitude of difference is less than that observed from the objective cognitive measure above (i.e., mini-mental state examination (MMSE) scores).

Figure 4:
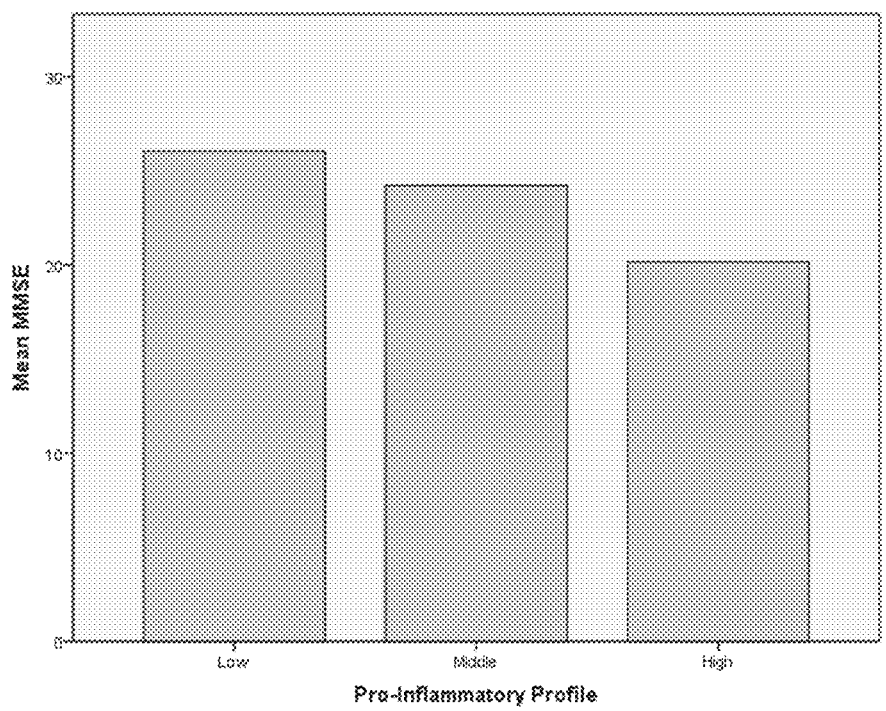
FIG. 4 is a graph that shows the linear decrease in cognitive functioning three different pro-inflammatory endophenotypes.
Figure 5:
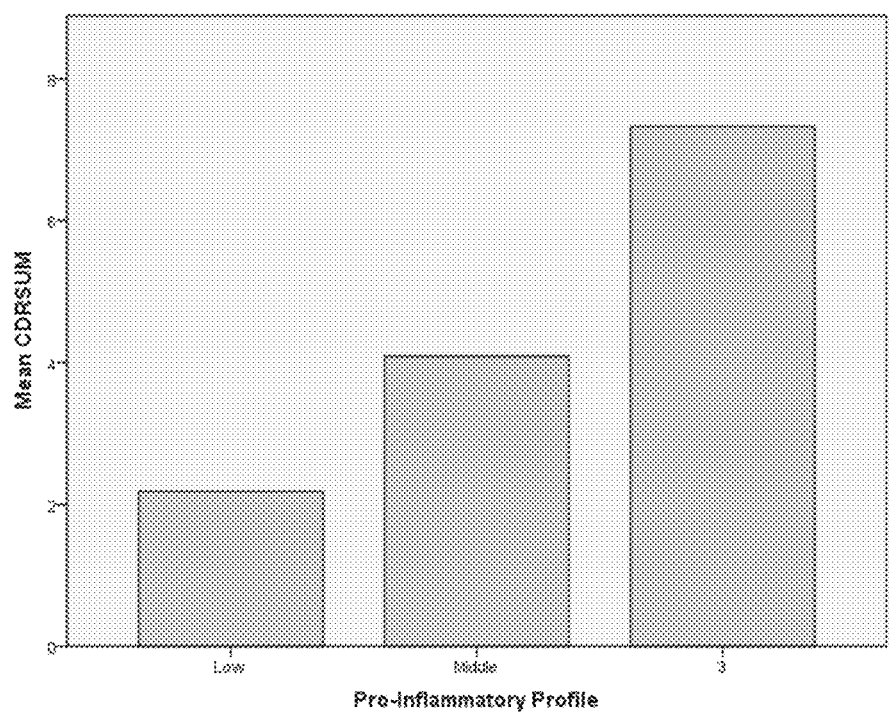
FIG. 5 shows the linear increase in disease severity on the pro-inflammatory endophenotypes among patients with Alzheimer's Disease.
Figure 6:
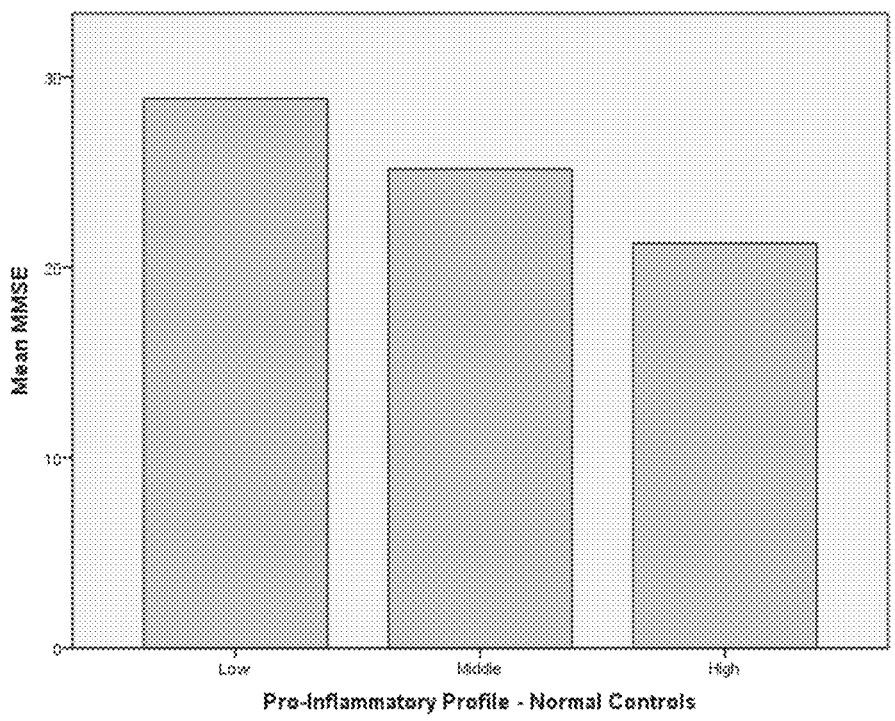
FIG. 6 shows the linear decline in baseline cognitive ability among non-demented normal controls as a function of the pro-inflammatory endophenotypes.

When examining baseline cognitive and disease severity markers from an independent cohort of AD cases and normal controls, the pro-inflammatory endophenotypes profile of the present invention clearly discriminated between patients' baseline characteristics. FIG. 4 shows a linear decrease in cognitive functioning (MMSE scores). FIG. 5 clearly demonstrates a linear increase in disease severity based on the pro-inflammatory profile among AD patients. FIG. 6 demonstrates the same linear decline in baseline cognitive ability (MMSE scores) among non-demented normal controls as a function of the pro-inflammatory profile.

Metabolic Endophenotype.

As discussed herein above, cognitive dysfunction and decline is a major source of morbidity and mortality in the U.S. Interestingly, metabolic dysfunction and diabetes is a common biological pathway that has been linked with each of these conditions as well as cognitive loss. Additionally, epidemiological studies suggest that midlife diabetes is a powerful risk factor for late-life cognitive loss and that diabetes is associated with increased neuropathological burden at autopsy. As a result of this literature, several clinical trials have been conducted using diabetes and metabolic medications to treat Alzheimer's disease, Mild Cognitive Impairment (MCI) (MCI; pre-AD) with some success and several ongoing studies. In fact, one group has begun a phase 3 trial of intranasal insulin as a therapy for MCI and early AD. While there has been some success, the therapeutic benefits have been modest and no prior work has been conducted to identify the specific patients with diabetes at greatest risk for cognitive loss. The novel method of the present invention was expressly developed as a companion diagnostic method (and personalized medicine approach) that identifies the sub-population of individuals who should be placed on diabetes/metabolic medications for cognitive enhancing benefits. The present invention can be implemented in clinical trials to best select patients most likely to benefit from the treatment thereby substantially reducing the sample sizes required.

The present inventors proposed a metabolic endophenotype among MCI and AD based on (1) prior work linking diabetes and metabolic disturbance to MCI and AD and (2) and the inventors' prior biomarker and clinical work among Mexican Americans[1-4]. The inventors also sought to characterize the metabolic endophenotype (MetEndo) among those diagnosed with MCI, AD and cognitively normal elders. Utilizing a multi-marker approach the present inventors have generated a metabolic endophenotypes (MetEndo). Those in the low end of the MetEndo (group 1) have minimal metabolic disturbance from a profile approach whereas those in the high end (group 3) have high levels of metabolic disturbance with all others remaining within the middle range (group 2). The inventors have found that the MetEndo predicts cognitive function and decline as well as risk for progression among those with metabolic dysfunction. The MetEndo should only be relevant for a subset of patients diagnosed with MCI and AD as the underlying neuropathology for AD is quite complex and there likely exists numerous endophenotypes. As disclosed herein the present inventors further demonstrated the existence and use of several endophenotypes including an inflammatory endophenotype[5,6], neurotrophic factor endophenotype[7,8] as well as a depressive endophenotype[9] and direct methods of treatment accordingly. In fact, the present invention can even be used to retrospectively analyze blood samples from previously conducted clinical trials to demonstrate that this approach (i.e., proinflammatory endophenotype) identifies a subgroup of AD patients that benefited significantly from a previously "failed" clinical trial. Therefore, the metabolic endophenotype can be utilized to treat specific subpopulations of AD patients to slow disease progression, reduce progression from MCI to AD in select subpopulations and even prevent cognitive loss among specific subpopulations of cognitive normal elders suffering from diabetes.

When examining prevalence of the MetEndo, the inventors found that 20% of MCI patients fit into the high end of the MetEndo as compared to 5% in the low end of the MetEndo. The rate increased to 25% in the high end when restricted to MCI cases diagnosed with diabetes. Those in the low end experienced greater cognitive dysfunction and increased disease severity at baseline (Table 2) and their pathology is likely driven largely by non-metabolic factors, namely Aβ (see table above; number 1=low MetEndo, 2=middle group; 3=high MetEndo). Of note, the MetEndo grouping is entirely independent of clinical characterization, but all patients were diagnosed with MCI. Interestingly, when examining cognitively normal elders (NC), there was also a significant difference in cognitive outcomes by the MetEndo groupings (see Table 3). Within the NC group, the high end of the MetEndo performed most poorly with regards to cognitive outcome variables. Therefore, there is a shift in cognitive ability from NC to MCI to AD (looked the same as MCI) as a function of MetEndo.

TABLE 2

Difference in cognitive outcomes by the MetEndo groupings

| | | | N | Mean | STD |
|---|---|---|---|---|---|
| MCI | CDRSUM | 1.00 | 3 | 1.17 | 1.155 |
| | | 2.00 | 4.5 | 1.10 | .802 |
| | | 3.00 | 14 | .75 | .325 |
| | | Total | 62 | 1.02 | .743 |
| | SS_Combined_LM_I | 1.00 | 3 | 4.67 | 3.215 |
| | | 2.00 | 44 | 8.39 | 3.301 |
| | | 3.00 | 13 | 10.00 | 2.708 |
| | | Total | 60 | 8.55 | 3.321 |
| | SS_Combined_LM_II | 1.00 | 3 | 7.00 | 3.606 |
| | | 2.00 | 44 | 8.86 | 3.481 |
| | | 3.00 | 13 | 10.77 | 3.032 |
| | | Total | 60 | 9.18 | 3.467 |

Based on this change, the high end of the MetEndo was used to show a significant association with the progression from NC to MCI and to AD. Over a 24 month follow-up period, the highest overall rate of overall progression was found among the high end of the MetEndo group (25%) as compared to 10% among the low MetEndo group and 20% in the middle group (progression in low and middle group likely due to non-metabolic factors).

Additionally, 18% of NCs in the high end of the MetEndo converted to MCI as compared to 7% of those in the low MetEndo group. A total of 34% of the MCI cases in the high MetEndo group progressed to AD within 24 months. The MetEndo was a significant predictor of progression from NC to MCI (AUC=0.63) and MCI to AD (AUC=0.60). Interestingly, 42% of the low end of the MetEndo progressed to AD over 24 months. This is likely due to the fact that (1) baseline cognition was lower in this group, and (2) the underlying pathology is loaded heavily to Aβ and these patients would benefit best from therapeutic agents targeting that mechanism specifically. Therefore, this method can be used for screening into the large-scale Aβ prevention trials (e.g. an A4 trial).

TABLE 3

| NC | | | | | |
|---|---|---|---|---|---|
| | | | N | Mean | STD |
| CDRSUM | | 1.00 | 9 | .06 | .167 |
| | | 2.00 | 104 | .03 | .250 |
| | | 3.00 | 32 | .11 | .535 |
| | | Total | 145 | .05 | .330 |
| SS_Combined_LM_I | | 1.00 | 9 | 10.33 | 3.905 |
| | | 2.00 | 103 | 10.17 | 3.784 |
| | | 3.00 | 31 | 9.29 | 3.466 |
| | | Total | 143 | 9.99 | 3.718 |
| SS_Combined_LM_II | | 1.00 | 9 | 11.22 | 2.587 |
| | | 2.00 | 103 | 11.45 | 3.165 |
| | | 3.00 | 31 | 10.26 | 3.109 |
| | | Total | 143 | 11.17 | 3.138 |

Neurotrophic Endophenotype.

Figure 7:
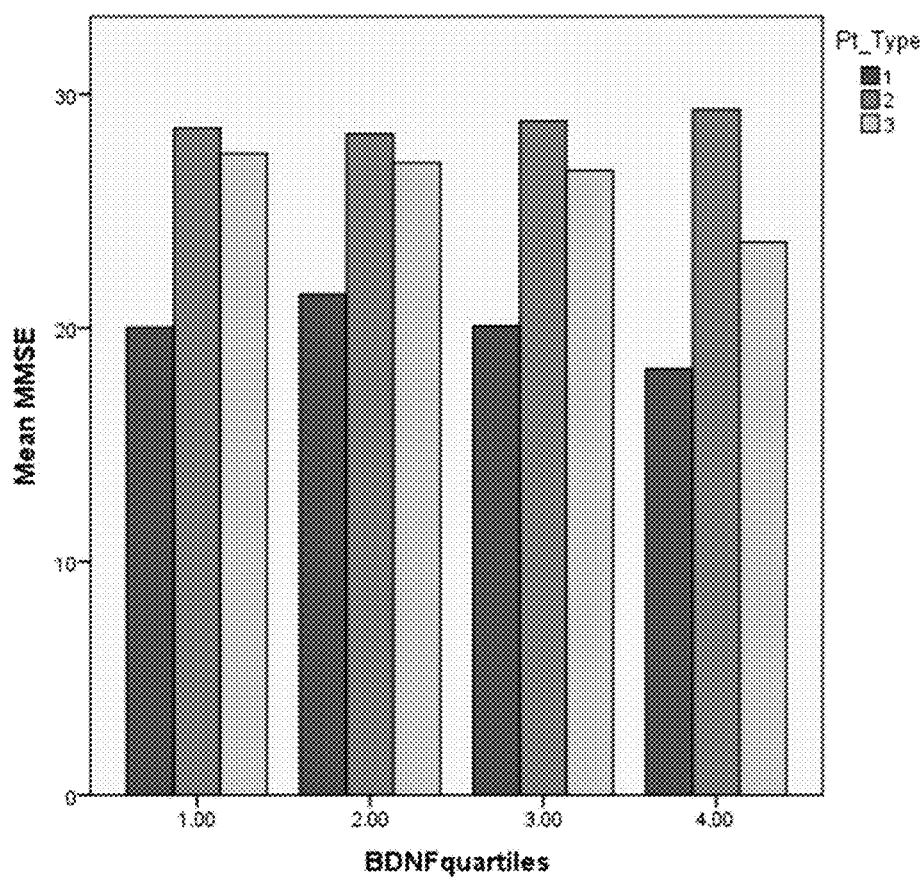
FIG. 7 shows that global cognitive ability (MMSE scores) varies as a function of BDNF levels by patient type (1=Alzheimer's disease, 2=normal control, 3=mild cognitive impairment) for a neurotrophic endophenotype.

A neurotrophic endophenotype was used to evaluate and treat cognitive loss/Alzheimer's disease (AD). The inventors have shown that neurotrophic factors, such as brain derived neurotrophic factor (BDNF) could potentially be a biomarker of Alzheimer's disease presence. However, it was found that BDNF levels were not significant predictors of disease status. On the other hand, BDNF levels were significantly related to memory performance among those diagnosed with AD. It is shown herein that neurotrophic factors (i.e., BDNF, NGF, TN-3, CNTF, GDNF, LIF, and GGF) can be used to identify a subset of individuals at risk for cognitive loss specifically related to this biological system. As such, knowledge of where someone falls within this specific endophenotype will guide a specific therapy for preventing and/or treating cognitive loss. It is shown herein that by simply using BDNF levels, one can clearly demonstrate different cognitive abilities among those with and without cognitive dysfunction. In FIG. 7, it is evident that global cognitive ability (MMSE scores) varies as a function of BDNF levels by patient type (1=Alzheimer's disease, 2=normal control, 3=mild cognitive impairment).

Additionally, when examined across cognitive test scores, a clear pattern emerged. Table 4 shows that, specifically, among those with cognitive loss (AD or MCI) higher score on the neurotrophic endophenotype (range 1-4 with 4 being high levels) are associated with poorer cognitive scores and more advanced disease severity among those with cognitive loss (MCI and AD). On the other hand, higher neurotrophic endophenotype score (i.e. 4) is associated with better cognitive functioning among those who are cognitively normal. This shows that there is a shift in the importance of neurotrophic factors as an elder transitions from normal elder to cognitively impaired. By way of explanation, but in no way a limitation of the present invention, this paradoxical finding of higher BDNF levels being associated with poorer memory abilities may be due to a compensatory effect[3]. That is, the brain is producing higher levels of neurotrophic factors in an effort to compensate for accumulating neuropathology. In fact, this is similar to the findings and hypothesis that led to the eventual FDA approval of several cholinesterase inhibitors for the treatment of AD.

TABLE 4

Neurotrophic endophenotypes.

| | PtTypeDesc | | N | Mean | Std. Deviation |
|---|---|---|---|---|---|
| AD | MMSE | 1.00 | 47 | 20.02 | 5.435 |
| | | 2.00 | 43 | 21.44 | 4.295 |
| | | 3.00 | 74 | 20.09 | 5.626 |
| | | 4.00 | 118 | 18.25 | 6.384 |
| | | Total | 282 | 19.52 | 5.844 |
| | CDRSUM | 1.00 | 46 | 5.33 | 3.453 |
| | | 2.00 | 43 | 6.59 | 3.497 |
| | | 3.00 | 76 | 7.29 | 4.247 |
| | | 4.00 | 117 | 8.39 | 4.347 |
| | | Total | 282 | 7.32 | 4.190 |
| | SS_Cowat | 1.00 | 40 | 6.63 | 3.712 |
| | | 2.00 | 40 | 6.53 | 2.736 |
| | | 3.00 | 69 | 6.99 | 3.127 |
| | | 4.00 | 99 | 6.71 | 3.444 |
| | | Total | 248 | 6.74 | 3.284 |
| | SS_Combined_LM_I | 1.00 | 32 | 3.94 | 2.199 |
| | | 2.00 | 35 | 3.74 | 2.501 |
| | | 3.00 | 57 | 4.23 | 2.521 |
| | | 4.00 | 91 | 3.47 | 2.218 |
| | | Total | 215 | 3.79 | 2.350 |

TABLE 4-continued

Neurotrophic endophenotypes.

| | PtTypeDesc | | N | Mean | Std. Deviation |
|---|---|---|---|---|---|
| | SS_Combined_LM_II | 1.00 | 32 | 4.50 | 2.627 |
| | | 2.00 | 35 | 3.57 | 1.720 |
| | | 3.00 | 57 | 3.91 | 1.994 |
| | | 4.00 | 89 | 3.30 | 1.774 |
| | | Total | 213 | 3.69 | 2.004 |
| | SS_Combined_VR_I | 1.00 | 28 | 4.50 | 2.365 |
| | | 2.00 | 28 | 5.00 | 3.151 |
| | | 3.00 | 54 | 5.20 | 2.757 |
| | | 4.00 | 98 | 4.08 | 2.903 |
| | | Total | 208 | 4.55 | 2.857 |
| | SS_Combined_VR_II | 1.00 | 28 | 5.61 | 2.217 |
| | | 2.00 | 28 | 4.86 | 2.068 |
| | | 3.00 | 54 | 4.63 | 2.095 |
| | | 4.00 | 96 | 4.79 | 2.419 |
| | | Total | 206 | 4.87 | 2.269 |
| MCI | MMSE | 1.00 | 102 | 27.46 | 2.349 |
| | | 2.00 | 64 | 27.06 | 2.429 |
| | | 3.00 | 59 | 26.73 | 2.658 |
| | | 4.00 | 3 | 23.67 | 4.509 |
| | | Total | 228 | 27.11 | 2.515 |
| | CDRSUM | 1.00 | 102 | .92 | .572 |
| | | 2.00 | 64 | 1.10 | .851 |
| | | 3.00 | 59 | 1.58 | 1.115 |
| | | 4.00 | 3 | 1.67 | 1.041 |
| | | Total | 228 | 1.15 | .867 |
| | SS_Cowat | 1.00 | 102 | 8.21 | 2.963 |
| | | 2.00 | 62 | 8.19 | 3.067 |
| | | 3.00 | 59 | 8.76 | 3.461 |
| | | 4.00 | 3 | 4.33 | 2.517 |
| | | Total | 226 | 8.30 | 3.148 |
| | SS_Combined_LM_I | 1.00 | 94 | 8.68 | 3.024 |
| | | 2.00 | 57 | 7.95 | 3.281 |
| | | 3.00 | 44 | 7.14 | 3.130 |
| | | 4.00 | 3 | 5.33 | 4.041 |
| | | Total | 198 | 8.08 | 3.189 |
| | SS_Combined_LM_II | 1.00 | 94 | 9.00 | 3.059 |
| | | 2.00 | 57 | 8.70 | 3.600 |
| | | 3.00 | 44 | 7.20 | 3.218 |
| | | 4.00 | 3 | 3.33 | 2.082 |
| | | Total | 198 | 8.43 | 3.363 |
| | SS_Combined_VR_I | 1.00 | 102 | 8.49 | 3.414 |
| | | 2.00 | 64 | 8.08 | 3.204 |
| | | 3.00 | 59 | 8.27 | 3.741 |
| | | 4.00 | 3 | 5.67 | .577 |
| | | Total | 228 | 8.28 | 3.426 |
| | SS_Combined_VR_II | 1.00 | 102 | 8.93 | 2.840 |
| | | 2.00 | 64 | 9.17 | 2.925 |
| | | 3.00 | 58 | 8.24 | 3.570 |
| | | 4.00 | 3 | 4.67 | 1.155 |
| | | Total | 227 | 8.77 | 3.093 |
| NC | MMSE | 1.00 | 158 | 28.55 | 1.808 |
| | | 2.00 | 136 | 28.32 | 2.427 |
| | | 3.00 | 136 | 28.85 | 1.856 |
| | | 4.00 | 127 | 29.35 | 1.088 |
| | | Total | 557 | 28.75 | 1.898 |
| | CDRSUM | 1.00 | 158 | .00 | .040 |
| | | 2.00 | 136 | .04 | .279 |
| | | 3.00 | 136 | .01 | .074 |
| | | 4.00 | 127 | .00 | .044 |
| | | Total | 557 | .01 | .146 |
| | SS_Cowat | 1.00 | 154 | 9.36 | 3.122 |
| | | 2.00 | 133 | 8.52 | 3.507 |

TABLE 4-continued

Neurotrophic endophenotypes.

| PtTypeDesc | | N | Mean | Std. Deviation |
|---|---|---|---|---|
| | 3.00 | 134 | 9.74 | 3.640 |
| | 4.00 | 126 | 11.40 | 3.025 |
| | Total | 547 | 9.72 | 3.473 |
| SS_Combined_LM_I | 1.00 | 152 | 9.79 | 3.321 |
| | 2.00 | 130 | 9.78 | 3.311 |
| | 3.00 | 120 | 11.38 | 3.644 |
| | 4.00 | 116 | 13.15 | 3.116 |
| | Total | 518 | 10.91 | 3.611 |
| SS_Combined_LM_II | 1.00 | 152 | 11.11 | 3.037 |
| | 2.00 | 129 | 10.95 | 2.904 |
| | 3.00 | 120 | 12.35 | 3.145 |
| | 4.00 | 116 | 13.66 | 2.690 |
| | Total | 517 | 11.93 | 3.137 |
| SS_Combined_VR_I | 1.00 | 147 | 9.53 | 3.482 |
| | 2.00 | 119 | 8.68 | 3.687 |
| | 3.00 | 118 | 10.47 | 3.858 |
| | 4.00 | 127 | 12.14 | 3.342 |
| | Total | 511 | 10.20 | 3.797 |
| SS_Combined_VR_II | 1.00 | 147 | 11.46 | 3.048 |
| | 2.00 | 119 | 10.72 | 3.045 |
| | 3.00 | 118 | 12.06 | 3.565 |
| | 4.00 | 127 | 13.28 | 3.196 |
| | Total | 511 | 11.88 | 3.332 |

Depressive Endophenotype

There is long-standing literature demonstrating the negative impact of depression on cognitive health among elders[23] with comorbid depression and cognitive dysfunction leading to greater impairment in activities of daily living as well as decreased quality of life[24,26]. However, identification of the specific patients suffering from depression most likely to experience cognitive dysfunction has remained elusive. The present inventors analyzed data from two independent cohorts, Project FRONTIER and the Texas Alzheimer's Research & Care Consortium (TARCC), to generate and cross-validate the depressive endophenotype of MCI/AD[17].

Depressive Endophenotype Identification. Development. First, the inventors randomly divided the Project FRONTIER cohort into two samples, the training (n=255, 52 MCI and 203 normal controls) and test sample (n=263, MCI n=60, control n=203). In the training sample, a series of $\chi^2$ analyses were conducted to identify which of the 30 items from the Geriatric Depression Scale were significantly endorsed more among the MCI cases. In the training sample, the following items were significantly endorsed more often among the MCI group than the normal cognition group: feeling of worse memory problems ($\chi^2$=12.39, p<0.001), feeling downhearted and blue ($\chi^2$=6.97, p=0.008), feeling worthless ($\chi^2$=5.58, p=0.02), frequently feel like crying ($\chi^2$=6.50, p=0.01), and trouble concentrating ($\chi^2$=7.82, p=0.005). Of note, a positive endorsement on each of these items is in the direction of presence of depression, therefore reverse scoring was not needed. The depressive endophenotype (DepE) was generated by summing the responses of each person on these 5 items.

Validation. Next, logistic regression was used to determine the risk of being diagnosed with MCI as a function of DepE scores within the test sample. DepE scores significantly increased risk for MCI diagnosis (odds ratio [OR] =2.04; 95% CI=1.54-2.69), which was the only significant predictor aside from age (OR=1.09; 95% CI=1.05-1.13) and education (OR=0.82; 95% CI=0.71-0.95). In a conditional stepwise forward logistic regression, age entered into the model first, followed by DepE scores; no other variables entered into the model. Of note, GDS total scores (minus DepE items) were not significantly related to MCI status with DepE scores entered into the model. Therefore, DepE scores and not global depression scores are specifically related to MCI risk. ApoEε4 genotype (the single strongest genetic risk for MCI and AD) did not enter the model.

Depressive Endophenotype Cross-Validation. Cross-Sectional Analyses. Next, the DepE was applied to the TARCC cohort. A logistic regression model was created with AD versus normal control as the outcome variable; age, gender, education, ApoEε4 presence (yes/no), GDS total score and DepE scores entered as the predictor variables. Age (OR=1.18, 95% CI=1.12-1.24, p<0.001), ApoEε4 status (OR=2.42, 95% CI=1.13-5.19, p=0.02) and the DepE scores (OR=2.49, 95% CI=1.40-4.43, p=0.002) were the only significant predictors of AD status. In the forward conditional stepwise logistic regression, the order of entry into the model was age, DepE scores (before ApoEε4 genotype), and ApoEε4 status. DepE score alone was a significant predictor of AD status using receiver operating characteristic (ROC) curve analysis (Area Under the Curve [AUC]=0.74 (95% CI=0.68-0.81), p<0.001). Longitudinal Analyses. Baseline DepE scores were also significantly related to global cognitive decline (MMSE scores) and increased disease progression (Clinical Dementia Rating scores) longitudinally[17]. The inventors also analyzed data from the Western Australia Memory Study cohort. This cohort included cognitively normal adults and elders being followed longitudinally to identify factors associated with cognitive loss. Among those ages 65 and above, elevations in DepE scores were significantly related to poorer cognitive functioning (i.e. below the mean of the cohort) (OR=1.53; 95% CI=1.01-2.32, p=0.04). Among those 70 and above, elevations in DepE scores were the single strongest risk for poorer cognitive functioning (OR=2.23, 95% CI 1.12-4.40, p=0.02) with age nor education being significant.

Figure 8:
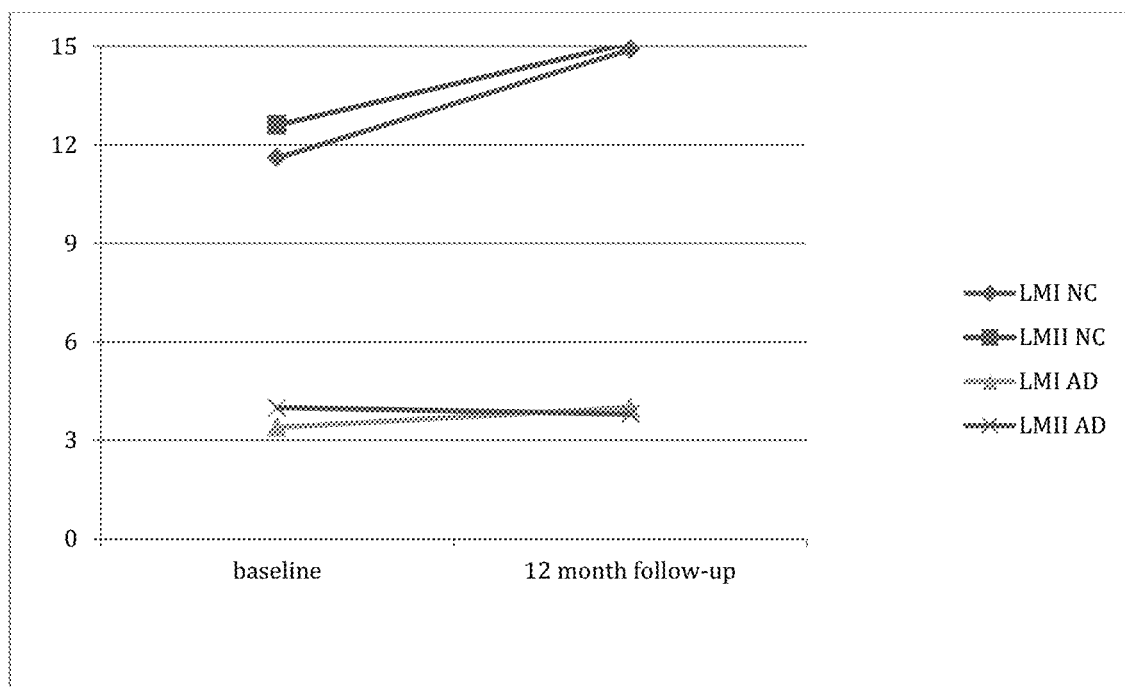
FIG. 8 shows the change in memory abilities (LM) scores for (LM) by AD vs. Controls—All patients DE scores were high T1 and normal T2. The vertical axis is reflective of scale score points on the Wechsler Memory Scale—Logical Memory Subtest (LMI=immediate memory; LMII=delayed verbal memory); NC=normal control; AD=Alzheimer's disease, for a depressive endophenotype.

More recent analyses were conducted to determine (1) the impact of improvement in DepE scores on cognition over time and (2) further cross-validation of DepE among non-demented older adults in another independent study. Preliminary analyses were also conducted to determine the impact of change in DepE scores over time specifically on memory scores using WMS Logical Memory I and II. Normal was considered to be a DepE score=0-1 with any score>=2 being considered high. The groups were as follows. FIG. 8 is a graph that depicts change in immediate (LMI) and delayed (LMII) verbal memory among normal controls (NC) and AD cases over a 12-month period. While improvement in DepE scores did not result in a change in memory abilities among AD cases, there was a tremendous improvement in memory scores (immediate and delayed) among normal controls who experienced an improvement in DepE scores. In fact, non-demented elders who were elevated on DepE scores obtained baseline memory scale scores a full standard deviation (i.e. 3 scale score points) below those without an elevation in DepE scores. However, improvement in DepE scores over 12-months resulted in an improvement in immediate and delayed memory scores of 1 full standard deviation (3 scale score points) equivalent to the level of cognitively normal elders that did not show baseline DepE elevations. Importantly, these findings show that intervening before the diagnosis of AD is warranted and the DepE offers a way of identifying those cognitively normal or mild cognitive impairment (MCI) patients that will experience cognitive improvement from antidepressant treatment. This cognitive improvement would be due to depression associated with TBI, Parkinson's disease, multiple sclerosis, diabetes and many other medical conditions as well as depression independent of or in absence of other medical conditions.

Method for Identifying Patients for a Personalized Medicine Approach to Treating and Preventing Cognitive Loss.

Cognitive dysfunction and decline is a major source of morbidity and mortality in the U.S. Cognitive dysfunction is associated with greater health care cost, decreased treatment compliance, lost wages (patient and family), decreased productivity, poorer quality of life and gradual loss of independence. The most prominent form of cognitive loss is dementia of the Alzheimer's type; however, cognitive loss is also associated with traumatic brain injury (TBI), multiple sclerosis (MS), Parkinson's disease (PD), depression, schizophrenia, as well as many other disorders/diseases. Interestingly, inflammation is a common biological pathway that has been linked with each of these conditions as well as cognitive loss. The inventors have previously generated a blood-based method for (1) identification of Alzheimer's Disease and (2) detecting and discriminating between neurodegenerative diseases. However, these data also suggest that the biological algorithms and endophenotypes generated can also distinguish cognitive ability among those within the pre-AD stage of Mild Cognitive Impairment as well as among cognitively normal adults and elders. The methods taught herein can also identify those at greatest risk for cognitive decline. A purpose of the current invention is the introduction of a method for selecting patients into trials aimed at preventing and/or treating cognitive loss based on the disclosed endophenotype methods.

The primary method for selecting patients into clinical trials is on disease diagnosis. However, most diseases have incredibly complex etiologies (e.g. diabetes, heart disease, Alzheimer's disease, depression). The approach begins with the patient presenting with a diagnosis of cognitive loss. Therefore, the current methods are directed towards the diagnosis of cognitive loss, independent of disease state. The cognitive loss may be due to any number of underlying conditions including, but not limited to Alzheimer's disease, Parkinson's disease, Multiple Sclerosis, stroke, other neurodegenerative or neurological disease, depression or other affective disturbance, diabetes and other metabolic disturbance, heart disease, and thyroid disease. Once identified as having or at risk for cognitive loss, the personalized medicine approach can also be used.

When examining baseline cognitive and disease severity markers for those diagnosed with Alzheimer's disease and normal controls, the present inventors have shown that inflammatory profiles can discriminate between cognitive abilities.

Figure 9:
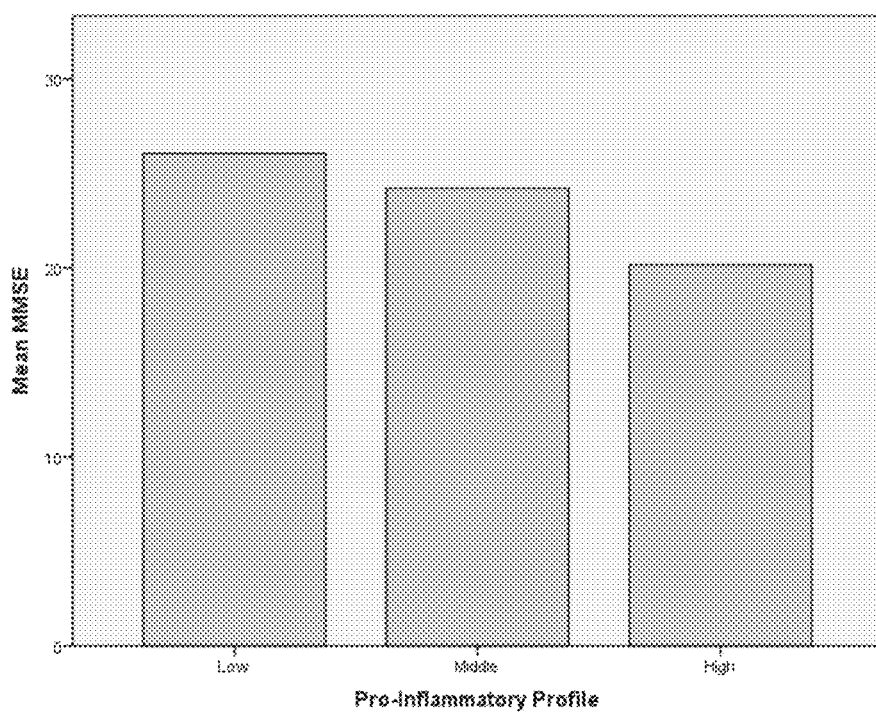
FIG. 9 shows a linear decrease in cognitive functioning (MMSE scores).
Figure 10:
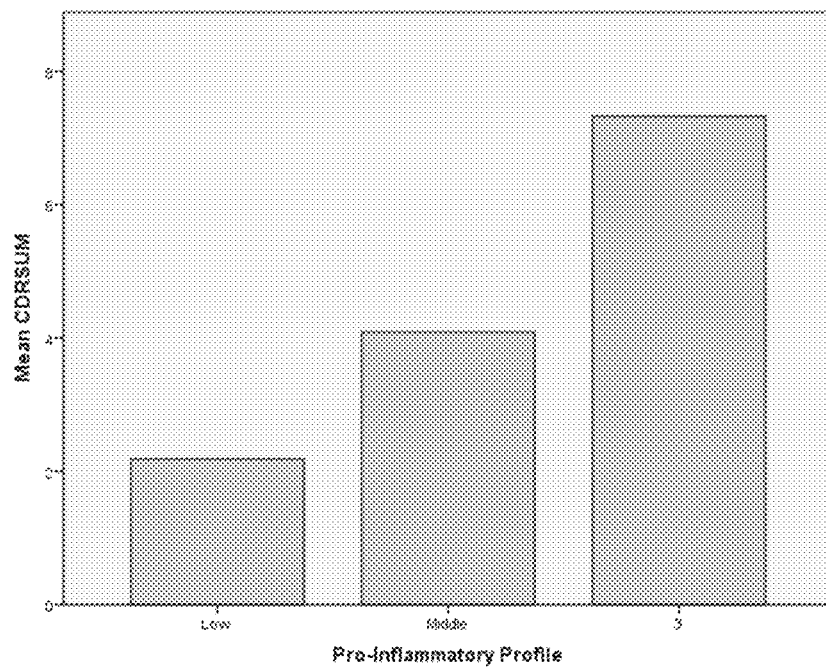
FIG. 10 demonstrates a linear increase in disease severity based on the pro-inflammatory profile among AD patients.
Figure 11:
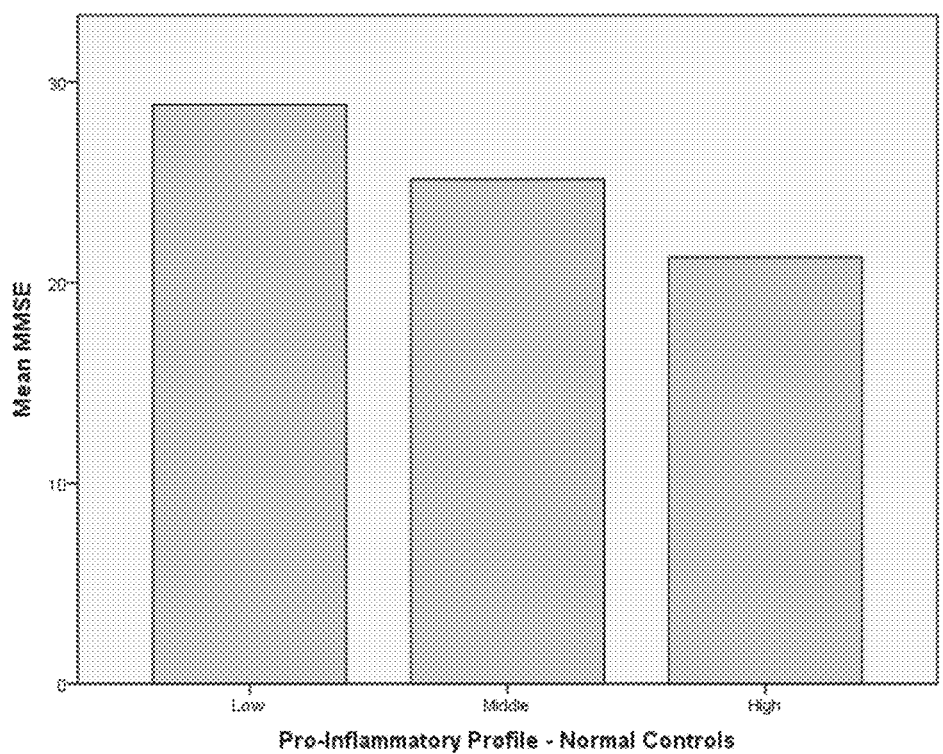
FIG. 11 demonstrates the same linear decline in baseline cognitive ability (MMSE scores) among non-demented normal controls as a function of the pro-inflammatory profile.

FIG. 9 shows a linear decrease in cognitive functioning (MMSE scores). When examining baseline cognitive and disease severity markers for those diagnosed with Alzheimer's disease and normal controls, the inventors show herein that inflammatory profiles can discriminate between cognitive abilities. FIG. 9 shows a linear decrease in cognitive functioning (MMSE scores). FIG. 10 demonstrates a linear increase in disease severity based on the pro-inflammatory profile among AD patients. FIG. 11 demonstrates the same linear decline in baseline cognitive ability (MMSE scores) among non-demented normal controls as a function of the pro-inflammatory profile.

Figure 12:
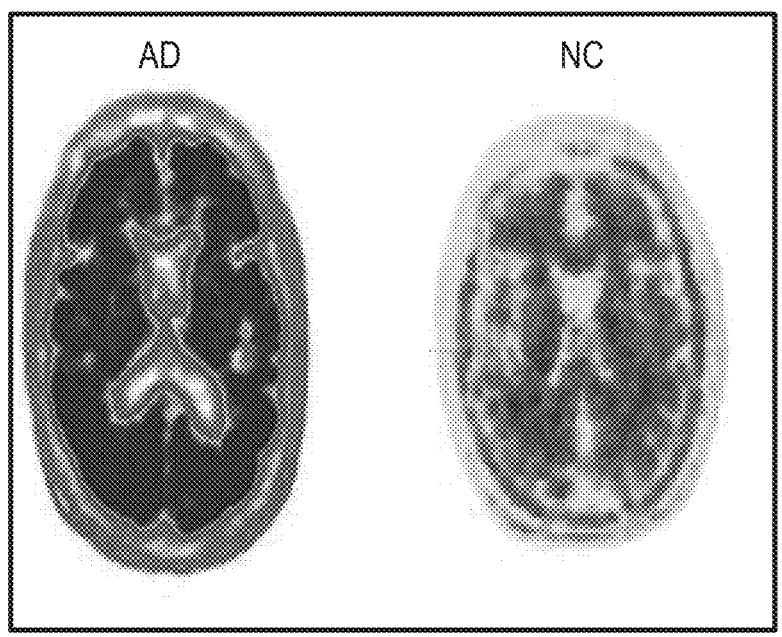
FIG. 12 shows the link between the blood-based biomarker system and the presence of beta amyloid (A$\beta$) in those with and without cognitive impairment (AD n=2, MCI n=2, control n=2) (change in management delayed the scans).

FIG. 12 shows the link between the blood-based biomarker system and the presence of beta amyloid (Aβ) in those with and without cognitive impairment (AD n=2, MCI n=2, control n=2) (change in management delayed the scans). In this example, 4 of the 6 participants were positive for Aβ (2 AD, 1 MCI & 1 control) when the test was conducted. It was found that the blood-based biomarker system was 100% accurate in detecting Aβ positivity.

These results demonstrate that the systematic approach of the present invention accurately detects Mild Cognitive Impairment. Next, the inventors assayed 269 samples (normal control n=88, MCI n=57, AD n=124) to: (1) detect amnestic versus non-amnestic MCI and (2) discriminate MCI from AD. The biomarker profile accurately detected amnestic MCI (AUC=0.94, SN=0.97, SP=0.87). The same methodology was slightly less accurate in detecting non-amnestic MCI (AUC=0.70, SN=0.70, SP=0.66) though the incorporation of minimal cognitive testing significantly increased the accuracy (see below). Thus, the biomarker profile plus Trail Making Test part B improved accuracy in detecting amnestic MCI (AUC=0.95) and non-amnestic MCI (AUC=0.85). In one non-limiting example of discriminating MCI from AD, it was important to split the process by APOE4 genotype. The present invention was most accurate at distinguishing MCI from AD among APOE4 non-carriers (AUC=0.80, SN=0.85, SP=0.74) as compared to APOE4 carriers (AUC=0.76, SN=0.44, SP=0.90). However, inclusion of animal naming increased overall accuracy to 0.86 among non-APOE4 carriers and to 0.89 among APOE4 carriers.

The present invention can also be used to identify cognitive loss among those without frank impairment. In fact, the present invention was 100% accurate in detecting those "cognitively normal" elders who had poorer memory abilities (i.e. <1.0 sd on story memory).

The present invention also allows the prediction of future risk for cognitive dysfunction. First, outlined above is the data where the present invention was used to identify amyloid-beta positivity. Having amyloid-beta within the brain is a very strong risk factor for future cognitive decline. Next, biomarkers of metabolic dysfunction were used to demonstrate the efficacy of the methods taught herein to predict cognitive loss over time. The metabolic risk score predicted future cognitive loss among those who were cognitively normal at baseline as well as predicted risk for progression from MCI to AD.

Therefore, these data demonstrate that the present invention can be used to identify individuals with or at risk for cognitive loss using an overall profile approach as well as specific endophenotype approaches (e.g. inflammation, metabolic dysfunction, neurotrophic system, depressive endophenotype).

Method for Producing Prognostic Models of Patient Responses to Therapeutic Molecules.

Billions of dollars has been spent on "failed" clinical trials. A key flaw to the current design of most trials is the selection of patient populations. Specifically, patients are typically screened into trials based on a heterogeneous disease classification rather than the specific biology of the drug and the patient's baseline biological profile. As an example, Alzheimer's disease clinical trials recruit based on a clinical diagnosis of NINDS-ADRDA (or newer NIA-AA) criteria "Probable Alzheimer's Disease" without regard to any specific underlying biological mechanism linked to AD itself. Because of the "one-size-fits-all" approach to many clinical trials seeking a single cure/treatment for a complex disease process, there are thousands of previously conducted "failed" trials with potentially useful therapeutic molecules that will not make it to patients who would benefit most by those particular medications. It is also well-known that all trials have responders and non-responders, but the trials are designed to look for group-level effects rather than sub-populations.

The identification of patients most likely to be responders, non-responders and adverse responders to therapeutic agents has tremendous potential for revolutionizing medical practice. Currently, the majority of clinical trials enroll patients by heterogeneous disease categorizations (e.g. Alzheimer's disease, Multiple Sclerosis, Parkinson's disease, COPD, chronic kidney disease) rather than sub-categorizations of patients most likely to respond to a given therapy. A method for the generation of companion diagnostic tools explicitly designed to identify those patients most likely to benefit is shown herein. It has the further advantage that the present invention has no impact (negative consequences) on previously conducted clinical trials. Thus, this method (outlined briefly below) can then be used to: (1) target medications to specific patient populations and even (2) generate new clinical trials that enroll specific patients most likely to benefit from the specific drug itself.

Broadly, the methods generated for use here monitor dysfunction within multiple biological systems including inflammation, neurotrophic factors, and metabolic dysfunction. Other systems can be also be targeted to the specific therapeutic molecule as deemed appropriate for a particular candidate drug. These systems are monitored via proteomic analyses though genomic (as well as other) markers can be incorporated as needed for the particular compound. It is important to note that this is not a single-marker approach. The superiority of multi-marker approaches when considering proteomic analyses as applied to complex diseases has already been shown hereinabove. Therefore, overall dysfunction of the system is monitored rather than the method being skewed by any single marker. With appropriate sample sizes within each individual trial analyzed, the systems are monitored via advanced bioinformatics (e.g. structural equation modeling, random forest analysis, support vector machines).

Once the specific systems are selected for monitoring and samples identified, the approach can be applied in a variety of ways. However, the optimal approach is as follows, which requires multiple previously-conducted trials (e.g. Phase 2a, Phase 2b, Phase 3).

Step 1. Generation of the prediction model. This approach will take 2 forms:
(1) a priori definition of the systems and how they will predict treatment response (positive, negative and no response); (2) a theoretical discovery of the optimal prediction algorithm for detection of responders, non-responders and adverse responders. This entire step takes place in the initial clinical trial completely independent of all other trials.

Step 2. Application and refinement of the model. Once the model is generated from Step 1, it is applied blindly to the second clinical trial to predict outcomes. Next, the process in Step 1 is used again in this second trial to further refine the predictive algorithm.

Step 3. Validation of the model. Once the model has been generated and refined, it is then applied to the first Phase 3 clinical trial to determine the efficacy of the model in predicting treatment responders, non-responders and adverse responders. If a second Phase 3 trial is available, the model is applied again with further refinement if necessary.
1. The outcome variables of treatment response are open. For example, for MS the outcome can be relapse rates, but also quality of life, daily living ability, depression rates (depressive endophenotypes), cognitive ability (again the depressive endophenotype is useful here), or whatever outcome of interest to the user.
2. The product at the end of the project is designed to be a companion diagnostic that can be used to (a) select patients for targeted therapy and/or (b) design a new clinical trial that specifically targets only those patients most likely to respond.

The current methodology provides a method for refining target populations to therapeutic molecules. Despite the fact that most therapeutic molecules do not make it through Phase 3 trials, many of these molecules have considerable impact for sub-populations of patients. However, a company cannot post hoc analyze a clinical trial and present that information to the FDA. On the other hand, the method taught herein provides a novel way for the identification of treatment responders, non-responders and adverse responders which can then be used to: (1) target specific patient populations with FDA approved drugs, as well as (2) design additional Phase 3 trials that will selectively enroll (and rule out) target populations to demonstrate efficacy of these therapeutic molecules.

Blood samples from a previously conducted clinical trial among AD patients was used. This trial was conducted by the Alzheimer's Disease Cooperative Study (ADCS, Aisen et al 2003, JAMA).

Baseline plasma samples were assayed using ECL for a range of inflammatory markers. The pro-inflammatory profile was generated using CRP and TNFα. The frequency of the low, middle (referent group) and high ends of the pro-inflammatory profile are presented in Table 5.

| | | | InfEndo3 | | | |
|---|---|---|---|---|---|---|
| | Arm2 | | Frequency | Percent | Valid Percent | Cumulative Percent |
| placebo | Valid | Low | 6 | 8.3 | 11.1 | 11.1 |
| | | Middle | 43 | 59.7 | 79.6 | 90.7 |
| | | High | 5 | 6.9 | 9.3 | 100.0 |
| | | Total | 54 | 75.0 | 100.0 | |
| | Missing | System | 18 | 25.0 | | |
| | Total | | 72 | 100.0 | | |
| treatment | Valid | Low | 7 | 9.1 | 11.1 | 11.1 |
| | | Middle | 46 | 59.7 | 73.0 | 84.1 |
| | | High | 10 | 13.0 | 15.9 | 100.0 |
| | | Total | 63 | 81.8 | 100.0 | |
| | Missing | System | 14 | 18.2 | | |
| | Total | | 77 | 100.0 | | |

Table 5 is a summary of the changes in MMSE scores over the 12 month period of the trial. The findings were as follows: Placebo group—(a) those in the low end of the pro-inflammatory profile were stable over 12 months (stable in disease severity and cognitive functioning) when compared to the high end and the referent group (i.e. middle group), (b) those in the high end declined significantly over 12 months when compared to the referent group and the low end of the pro-inflammatory profile.

Figure 13:
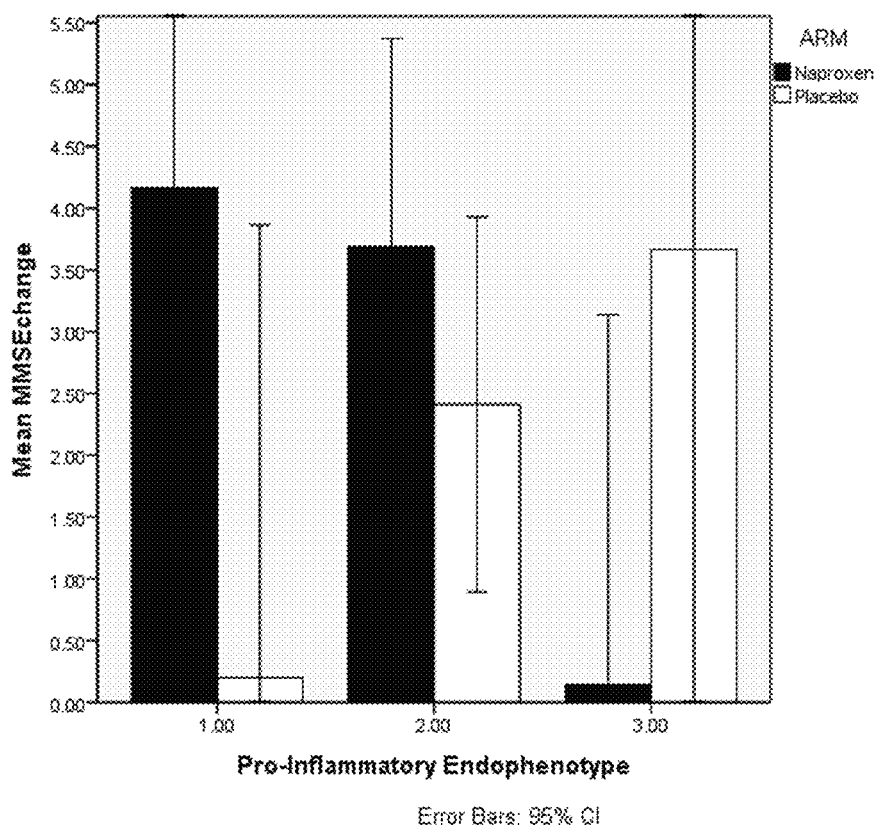
FIG. 13 is a graph that shows the results for the treatment group—(a) those in the low end of the pro-inflammatory profile (Group 1.00) who were treated with an anti-inflammatory drug declined significantly faster (i.e. disease severity and cognition) when compared to the referent group (i.e. middle group; Group 2.00)), (b) those in the high end (Group 3.00) were stable over 12 months when treated with an anti-inflammatory drug when compared to the low end of the pro-inflammatory profile and the referent group.

FIG. 13 shows the results for the treatment group—(a) those in the low end of the pro-inflammatory profile (group 1 in FIG. 13) who were treated with an anti-inflammatory drug declined significantly faster (i.e. disease severity and cognition) when compared to the referent group (i.e. middle group; group 2 in FIG. 13)), (b) those in the high end (group 3 in FIG. 13) were stable over 12 mo when treated with an anti-inflammatory drug when compared to the low end of the pro-inflammatory profile and the referent group.

Figure 14:
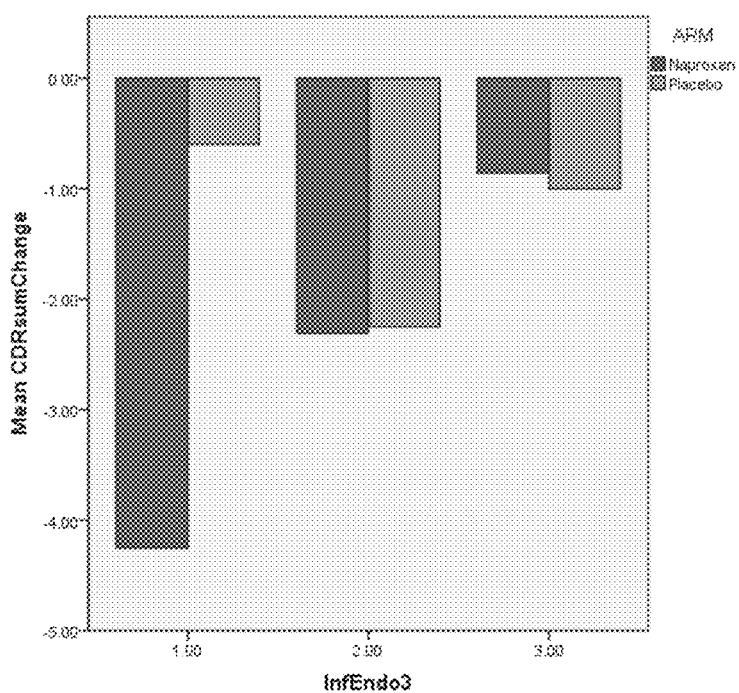
FIG. 14 is a graph that shows disease severity (i.e. CDR Sum of Boxes [CDRSum]) for the three Groups shown in FIG. 13 with treatment with an NAIDS (naproxen) or placebo.

When considering disease severity (i.e. CDR Sum of Boxes [CDRSum]), the same was found. See FIG. 14. Specifically, those in the low end of the pro-inflammatory profile who were treated with an anti-inflammatory drug progressed in disease severity more rapidly over 12 mo than any other group whereas those who were in that same biomarker-defined group declined minimally over 12 months if left untreated. On the other hand, those in the high end who were treated declined less than those who were untreated though the magnitude of difference is less than that observed from the objective cognitive measure above (i.e. MMSE scores).

These data demonstrate the effectiveness of the methods and now these methods will be applied to numerous other disease states (e.g. Multiple Sclerosis).

Association of Cognitive Impairment with Chronic Kidney Disease in Hispanics.

Over the last 45 years, the Hispanic population in the United States has increased six-fold thereby making it the fastest growing segment of the population [1]. Unfortunately, Hispanics experience a far greater incidence of end-stage renal disease (ESRD) than non-Hispanic whites. Data from the United States Renal Data System reveal that Hispanics have a 1.5 greater incidence of ESRD than non-Hispanic whites [2]. Despite a clear increase in the incidence of ESRD, the incidence of chronic kidney disease (CKD) in the Hispanic population is equal to or even less than that of non-Hispanic whites [3, 4]. This would suggest that chronic kidney disease progresses faster to ESRD in the Hispanic population. The reason for this disparity is unclear.

Analysis of data from both the National Health and Nutrition Examination Survey (NHANES) 1999-2008 and from the Northern California Kaiser Permanente health system, shows that Hispanics with diabetes have a greater level of urinary albumin excretion than non-Hispanic whites [5-7]. In the general CKD population, the degree of albuminuria has been clearly linked to progression of renal disease [8]. The greater degree of albuminuria in Hispanics may represent generalized endothelial dysfunction, which has been associated with mild cognitive impairment (MCI) [9]. Cognitive impairment has been linked to increased mortality in both the CKD and non-CKD population [10, 11]. MCI may effect heath literacy and lead to a decreased ability to adhere to preventative and therapeutic regimens [12].

Hispanics appear to be at greater risk for cognitive impairment than non-Hispanics [13]. In addition "established" risk factors for MCI (hypertension, obesity, dyslipidemia, and APOE4 genotype) have not been shown to be significant for Mexican-Americans [14]. Although it has been well established that CKD is a risk factor for cognitive decline in the general population [15-18], there are few published studies demonstrating that CKD in Hispanics is associated with cognitive impairment [19, 20]. These studies, however, utilized only general screening tools to assess cognitive decline.

There is a significant need to identify methods for the identification of CKD patients suffering from MCI as well as pre-MCI and new treatment regimes based on the result outcomes. The present study sought to address this need by examining the link between CKD and cognition/MCI among a community-dwelling cohort of Mexican Americans. In addition, the inventors determined if serum proteomic markers from the inventors' previously generated blood-profile of AD could be utilized to generate a blood-profile of CKD-related cognitive dysfunction.

Participants. Data from 437 participants (105 men and 332 women) from the Health & Aging Brain among Latino Elders (HABLE) study were analyzed. The HABLE study is an ongoing epidemiological study of cognitive aging among community-dwelling Mexican American individuals. The HABLE study used a community-based participatory research (CBPR) approach, which is a research methodology that involves partnering communities with scientific groups to conduct studies of human disease that is growing rapidly in terms of use and acceptance in the scientific community. The generation of locations for targeted CBPR recruitment was determined through analysis of zip codes in Tarrant County with the highest population density of Hispanic individuals. The research was conducted under an IRB approved protocol with each participant (and/or informants for cognitively impaired persons) providing written informed consent.

Study Design. Each participant underwent an interview (i.e., medical history, medications, health behaviors), detailed neuropsychological testing, blood draw, and medical examination (review of systems, Hachinski Ischemic Index scale, brief neurological screen). The neuropsychological battery consisted of tests of executive functioning (Trail Making Test [25], EXIT25, clock drawing [CLOX1] [26]), language (FAS and Animal Naming) [27], visuospatial skills (CLOX2 [26]), memory (Wechsler MemoryScale—$3^{rd}$ ed Logical Memory, Consortium for the Establishment of Registry for Alzheimer's Disease (CERAD) List Learning [27]) and attention (WMS-3 Digit Span [28]). Testing was completed in English or Spanish depending on the participant's preference. Raw scores were utilized in analyses. The current team has generated normative references for each of these tests for English- and Spanish-speaking Mexican Americans for diagnostic purposes (manuscripts in preparation). Cognitive diagnoses of mild cognitive impairment (MCI) were assigned according to Mayo Clinic criteria [29] by consensus review. Preliminary analyses were conducted on a subgroup of pre-MCI participants defined as normal controls with CERAD List Recall<1 standard deviation below the mean.

Blood collection and processing. Fasting bloods were drawn for clinical laboratory analyses. eGFR was calculated using the CKD-epi formula. Serum samples were also collected and stored in the biobank as follows: (1) serum samples were collected in 10 ml tiger-top tubes, (2) allowed to clot for 30 minutes at room temperature in a vertical position, (3) centrifuged for 10 minutes at 1300×g within one hour of collection, (4) 1.0 ml aliquots of serum were transferred into cryovial tubes, (5) Freezerworks™ barcode labels were firmly affixed to each aliquot, and (6) samples placed into −80° C. freezer within two hours of collection for storage until use in an assay.

Biomarker assays. All samples were assayed in duplicate via a multi-plex biomarker assay platform using electro-chemiluminescense (ECL) on the SECTOR Imager 2400A from Meso Scale Discovery (MSD; www.mesoscale.com). The MSD platform has been used extensively to assay biomarkers associated with a range of human diseases including AD [26-30]. ECL measures have well-established properties of being more sensitive and requiring less sample volume than conventional ELISAs [30], the gold standard for most assays. The markers assayed were generated as described hereinabove and cross-validated AD algorithm [21-24] and included: fatty acid binding protein (FABP3), beta 2 microglobulin, pancreatic polypeptide (PPY), sTNFR1, CRP, VCAM1, thrombopoeitin (THPO), α2 macroglobulin (A2M), exotaxin 3, tumor necrosis factor α, tenascin C, IL5, IL6, IL7, IL10, IL18, I309, Factor VII, TARC, SAA, and ICAM1.

Statistical analyses. The link between eGFR levels and neuropsychological outcomes was assessed via ANOVA (unadjusted models) and ANCOVA (covariates include age, gender, education). eGFR were divided into the following groups: <45, 45-59 and >=60 (ml/min/1.73 m$^2$). The link between serum biomarkers and MCI (and pre-MCI) status was examined via logistic regression (age, gender, education entered as covariates). All serum biomarkers were transformed using Box-Cox transformation.

The average age and education of the sample was 61.2 (sd=8.3; range=50-91) and 7.7 (sd=4.3; range=0-18), respectively. The average eGFR levels were 86.3 (sd=17.0; range=21-123). eGFR categories were broken down as follows: <45 (n=14), 45-59 (n=20) & >=60 (n=403). Those with eGFR>=60 were significantly younger than the other two groups with the lower eGFR groups not being significantly different from one another. See Table 6 for demographic characteristics of the cohort. A total of 83 participants were diagnosed as MCI.

In the unadjusted models, lower eGFR levels were associated with significantly poorer performance in the domains of global cognition (MMSE), memory (WMS-3 LM and CERAD Recall), executive functioning (EXIT25, CLOX1), processing speed (Trails A), visuospatial skills (CLOX2), and language (Animal Naming) (see Table 6). In the adjusted models, the <45 group performed significantly worse than the 45-59 & >=60 groups in the following domains: processing speed (Trail Making Test part A, F=14.1, p<0.001), executive functioning (CLOX1, F=4.5, p=0.01), visuospatial skills (CLOX2, F=4.8, p<0.009) and global cognitive functioning (MMSE, F=6.2, p=0.002). Additionally, the eGFR<45 group performed significantly worse than the eGFR>=60 group on delayed memory (CERAD List Recall, F=3.8, p=0.02). The individual mean I-J difference scores are shown in Table 7.

TABLE 6

Demographic characteristics and cognitive test data from HABLE sample

|  | Total Sample | eGFR <45 n = | eGFR = 45-59 n = | eGFR >=60 n = | p-value |
|---|---|---|---|---|---|
| Age | 61.3 (8.3) | 71.4 (8.1) | 68.9 (8.5) | 60.4 (7.7) | *<0.001 **ns |
| Education | 7.7 (4.3) | 6.7 (5.7) | 7.6 (3.4) | 7.7 (4.3) | Ns |
| Gender (% female) |  | 76% | 75% | 64% |  |
| eGFR (60 mL/min/1.73 m2) | 86.3 (17.0) | 36.5 (7.5) | 52.1 (3.9) | 89.8 (12.3) |  |
| MMSE | 25.5 (4.0) | 21.5 (5.9) | 25.9 (2.5) | 25.7 (3.7) | *<0.001 **= 0.001 |
| Trails A | 63.6 (32.4) | 113.3 (53.8) | 65.9 (22.3) | 61.7 (30.6) | *<0.001 **<0.001 |
| Trails B | 161.3 (79.0) | 193.7 (84.9) | 198.4 (81.2) | 158.9 (78.4) | *ns **ns |
| WMS-3 LM2 | 10.0 (2.5) | 12.4 (11.7) | 17.7 (8.0) | 18.5 (8.9) | *=0.01 **ns |
| CERAD Recall | 4.8 (2.4) | 2.7 (2.3) | 3.3 (2.1) | 4.9 (2.3) | *=0.002 **ns |
| CLOX1 | 10.7 (2.5) | 8.2 (2.8) | 10.7 (2.1) | 10.9 (2.4) | *<0.001 **= 0.004 |
| CLOX2 | 13.2 (1.7) | 7.4 (3.2) | 8.7 (1.9) | 10.0 (2.9) | *<0.001 **ns |
| FAS | 24.0 (10.4) | 21.5 (14.9) | 21.9 (11.4) | 24.3 (10.2) | *ns **ns |
| Animal Naming | 15.4 (4.7) | 12.0 (5.3) | 14.0 (4.1) | 15.6 (4.6) | *=0.006 **ns |
| EXIT25 | 9.8 (4.7) | 13.1 (4.5) | 10.9 (5.7) | 9.6 (4.6) | *=0.02 **ns |

NOTE:
all scores are raw values. For Trails A & B and EXIT25, higher scores are reflective of poorer performance whereas all other scores, higher scores are reflective of better performance.
*= eGFR <45 vs eGFR >=60;
**= eGFR <45 vs eGFR 45-59

In logistic regression model (age, education, glucose, hemoglobin and eGFR<60 entered into model), there was a trend towards eGFR<60 being associated with increased risk for MCI diagnosis that did not reach statistical significance likely due to sample size (OR=2.4, 95% CI=0.91-6.1, p=0.07). Interestingly, when the analyses were split by gender, eGFR<60 was significantly associated with increased risk for MCI among men (OR=9.6, 95% CI=1.3-74.3, p=0.03).

TABLE 7

Adjusted models of impact of eGFR on cognitive abilities

|  | eGFR <45 vs. eGFR = 45-59 I-J Difference (SD) | eGFR <45 vs. eGFR <=60 I-J Difference (p-value) | eGFR = 45-59 vs. eGFR >=60 I-J Difference (p-value) |
|---|---|---|---|
| MMSE | -2.6 (0.9) P = 0.005 | -4.0 P < 0.001 |  |
| Trails A | 36.9 (7.3) P < 0.001 | 43.9 (9.0) P < 0.001 | Ns |
| Trails B | Ns | Ns | Ns |
| WMS-3 LM2 | Ns | Ns | Ns |
| CERAD Recall | -1.4 (0.6) P = 0.03 | Ns | ns |
| CLOX1 | -1.7 (0.5) P = 0.005 | -2.01 (0.8) P = 0.006 | Ns |
| CLOX2 | -1.3 (0.4) | -1.2 (0.5) | Ns |

TABLE 7-continued

Adjusted models of impact of eGFR on cognitive abilities

| | eGFR <45 vs. eGFR = 45-59 I-J Difference (SD) | eGFR <45 vs. eGFR <=60 I-J Difference (p-value) | eGFR = 45-59 vs. eGFR >=60 I-J Difference (p-value) |
|---|---|---|---|
| | P = 0.002 | P = 0.02 | |
| FAS | Ns | Ns | Ns |
| Animal Naming | Ns | Ns | Ns |
| EXIT25 | Ns | Ns | Ns |

Next, the sample was split into those with eGFR<60 (MCI n=14) and those with eGFR>=60 (MCI n=68). In the logistic regression, a serum biomarker panel including only FVII, IL10, CRP, and FABP (no demographic variables were included in the model) was 93% accurate at identifying those individuals with MCI in the eGFR<60 group (sensitivity=86%, specificity=100%). The same set of markers was 85% accurate in detecting MCI in the eGFR>=60 group; however, this was biased by the 98% specificity but only 24% sensitivity. When examining only those with normal cognition, within the eGFR<60 group, 3 were classified as pre-MCI whereas 49 pre-MCI cases were identified within the eGFR>=60 group. The same algorithm was 100% correct at identifying the pre-MCI cases within the eGFR<60 group; however, none of the pre-MCI cases were correctly identified with the serum biomarkers in the eGFR>=60 group.

Numerous studies have clearly demonstrated the association between mild cognitive impairment and chronic kidney disease [15-18]. The decline in cognitive function affects all domains including executive function, verbal memory, visuospatial skills and attention span. The present invention demonstrates that the degree of cognitive impairment appears to be positively related to the severity of the renal disease. The worst the renal function the greater the cognitive deficit. In addition, cognitive impairment was found to progress more rapidly in patients with CKD, thus requiring more aggressive treatments and intervention.

The association of cognitive impairment with CKD is not surprising. Many of the same risk factors are responsible for both. Dementia in patients with CKD is of the vascular type and not Alzheimer's type. Yet even after adjusting for numerous cardiovascular risk factors, CKD remains an independent risk factor for cognitive impairment [19]. A common underpinning may be endothelial dysfunction, which is associated with both MCI and CKD [9]. Endothelial dysfunction can be caused by both inflammatory and metabolic determinants.

This study is the first to characterize the CKD-MCI relationship in a Mexican American population utilizing detailed neuropsychological testing. Previous studies showing the association of CKD with MCI used only general brief screening tests [19, 20]. For the first time the present invention permits a more complete understanding of MCI in Mexican Americans with CKD and the change in treatment regime due to these results obtained herein using the present invention. Cognitive decline worsens disease outcomes. Mexican Americans are the fasting growing segment of the U.S. population. They are also burdened with excess prevalence of end-stage renal disease. This excess risk may be due to socio-economic factors, poor health literacy, poorer diabetic control, lesser use of appropriate medications and worse blood pressure control [31-33]. At any stage of CKD Hispanics have higher levels of proteinuria than their non-Hispanic counterparts, suggesting a greater degree of endothelial dysfunction.

The present invention also demonstrates that a serum biomarker panel including FVII, IL10, CRP, and FABP is 93% accurate at identifying MCI among individuals with CKD (sensitivity=86%, specificity=100%). IL10 and CRP are markers of inflammation whereas FABP is strongly related to metabolic functioning. As shown hereinabove and in the inventors' prior work the biomarker profile of AD among Mexican Americans, the profile was heavily weighted towards metabolic factors (e.g. FABP, GLP-1, PPY) whereas it is shown herein that the biomarker profile of CKD-related MCI is largely inflammatory in nature. Therefore, the CKD-MCI profile is significantly different than the AD profile among Mexican Americans. Additionally, the CKD-MCI profile did not predict MCI among Mexican Americans not suffering from CKD. Interestingly, inflammation has been a key factor in the AD biomarker profile among non-Hispanics. This study further highlights the urgent need to refine the MCI nosology, specifically by recognizing the condition and then using that information to target the medical conditions with the correct treatment to impact cognition. As shown herein, the biomarker profile of MCI will vary significantly from one condition (e.g. diabetes-related MCI) to the next (i.e. CKD-related MCI) and interventions targeting cognition will likely need to be different as a result.

Because of the differences not only in the rate of progression of renal disease but also in the risk factors for MCI in Hispanics, it is important to study this ethnic group in more detail in order to validate this specific group of blood-based biomarkers. Such studies will enable us to better characterize the association between CKD and MCI and enable us to develop better targeted interventions to prevent or at least slow the progression of CKD and MCI.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

1. Gottesman, II, Shields J. Genetic theorizing and schizophrenia. British Journal of Psychiatry. 1973; 122(566): 15-30.
2. Gottesman, II, Gould T D. The endophenotype concept in psychiatry: etymology and strategic intentions. American Journal of Psychiatry. 2003; 160(4):636-645.
3. O'Bryant S E, Waring S C, Hobson V, et al. Decreased C-reactive protein levels in alzheimer disease. Journal of Geriatric Psychiatry and Neurology. 2010; 23(1):49-53.
4. O'Bryant S E, Xiao G, Barber R, et al. A serum protein-based algorithm for the detection of Alzheimer disease. Archives of Neurology. 2010; 67(9):1077-1081.
5. O'Bryant S E, Hobson V L, Hall J R, et al. Serum Brain-Derived Neurotrophic
Factor Levels Are Specifically Associated with Memory Performance among Alzheimer's Disease Cases. Dementia and Geriatric Cognitive Disorders. 2010; 31(1):31-36.
6. Johnson L A, Hall J R, O'Bryant S E. A Depressive Endophenotype of Mild Cognitive Impairment and Alzheimer's Disease. PLoS ONE. 2013; 8(7):e68848.
7. O'Bryant S E, Xiao G, Edwards M, et al. Biomarkers of Alzheimer's disease among Mexican Americans. Journal of Alzheimer's Disease. 2013; 34(4):841-849.
8. Janocko N J, Brodersen K A, Soto-Ortolaza A I, et al. Neuropathologically defined subtypes of Alzheimer's disease differ significantly from neurofibrillary tangle-predominant dementia. Acta Neuropathologica. 2012:1-12.
9. Braskie M N, Ringman J M, Thompson P M. Neuroimaging measures as endophenotypes in Alzheimer's disease. International Journal of Alzheimer's Disease. 2011.
10. During E H O R, Elahi F M, Mosconi L, de Leon, M J. The concept of FDG-PET endophenotype in Alzheimer's disease. Neurol Sci. 2011; 32:559-569.
11. N E-T. Gene expression endophenotypes: a novel approach for gene discovery in Alzheimer's disease. Molecular Neurodegeneration. 2011; 3(31):1-14.
12. Cruchaga C K J, Nowotny P, Bales K, Pickering E H, Mayo K, Bertelsen S, Hinrichs A, the ADNI initiative, Fagan A M, Holtzman D M, Morris J C, and Goate A M. Cerebrospinal fluit APOE levels: an endophenotype for genetic studies for Alzheimer's disease. Human Molecular Genetics. 2012; 2012.
13. O'Bryant S E, Hobson V, Hall J R, et al. Brain-derived neurotrophic factor levels in alzheimer's disease. Journal of Alzheimer's Disease. 2009; 17(2):337-341.
14. O'Bryant S E, Hobson V L, Hall J R, et al. Serum brain-derived neurotrophic factor levels are specifically associated with memory performance among Alzheimer's disease cases. Dementia and Geriatric Cognitive Disorders. 2011; 31(1):31-36.
15. O'Bryant S E, Xiao G, Barber R, et al. A blood-based algorithm for the detection of Alzheimer's disease. Dementia and Geriatric Cognitive Disorders. 2011; 32(1): 55-62.
16. O'Bryant S E, Xiao G, Barber R, et al. A Blood-Based Screening Tool for Alzheimer's Disease That Spans Serum and Plasma: Findings from TARC and ADNI. PLoS ONE. 2011; 6(12):e28092.

What is claimed is:

1. A method for treating a human subject with Alzheimer's Disease having a high proinflammatory endophenotype, the method comprising:
    obtaining a blood sample from the human subject with Alzheimer's disease;
    measuring the protein expression levels of tumor necrosis factor-alpha (TNFα), IL-5, IL-6, and C-reactive protein (CRP) biomarkers in the blood sample;
    applying an algorithm to the measured protein expression levels, the algorithm generating an endophenotype score based on a comparison of the measured protein expression levels to reference levels;

identifying the human subject with Alzheimer's Disease as having a high proinflammatory endophenotype profile based on the endophenotype score; and administering an anti-inflammatory drug treatment to the identified human subject;

wherein the algorithm is selected from a machine learning algorithm, a clustering algorithm, and a combination thereof.

2. The method of claim 1, wherein the machine learning algorithm is selected from random forest or support vector machines.

3. The method of claim 1,
wherein the blood sample is a whole blood or a plasma sample, and
wherein the biomarkers are measured by at least one method selected from an immunoassay, an enzymatic activity assay, fluorescence detection, chemiluminescence detection, electrochemiluminescence detection and patterned array, antibody binding, fluorescence activated sorting, detectable bead sorting, antibody array, microarray, enzymatic array, receptor binding array, solid-phase binding array, liquid phase binding array, fluorescent resonance transfer, and radioactive labeling.

4. The method of claim 1, wherein measuring the protein expression level of proinflammatory biomarkers in the blood sample further comprises measuring the protein expression level of proinflammatory biomarker IL-10 in the blood sample.

5. The method of claim 1, wherein the anti-inflammatory drug is selected from NSAIDs, non-selective NSAIDs, selective NSAIDs, steroids, glucocorticoids, Immune Selective Anti-Inflammatory Derivatives (ImSAIDs), anti-TNF medications, anti-IL5 drugs, and CRP-lowering agents.

6. The method of claim 1, wherein the anti-inflammatory drug is selected from NSAIDs, non-selective NSAIDs, and selective NSAIDs.

7. The method of claim 1, wherein the anti-inflammatory drug consists of non-selective NSAIDs.

8. The method of claim 1, wherein the clustering algorithm is selected from factor analysis or principal component analysis.

* * * * *